US011559618B2

(12) United States Patent
Testani et al.

(10) Patent No.: US 11,559,618 B2
(45) Date of Patent: *Jan. 24, 2023

(54) FORMULATIONS AND METHODS FOR DIRECT SODIUM REMOVAL IN PATIENTS HAVING SEVERE RENAL DYSFUNCTION

(71) Applicant: Sequana Medical NV, Ghent (BE)

(72) Inventors: Jeffrey Testani, Guilford, CT (US); Christopher McIntyre, Ontario (CA); Ian Crosbie, London (GB); Oliver Goedje, Strasslach (DE)

(73) Assignee: Sequana Medical NV, Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/661,737

(22) Filed: May 2, 2022

(65) Prior Publication Data
US 2022/0257843 A1    Aug. 18, 2022

Related U.S. Application Data

(63) Continuation-in-part of application No. 17/174,855, filed on Feb. 12, 2021, which is a continuation of application No. 15/985,598, filed on May 21, 2018, now Pat. No. 10,918,778.

(60) Provisional application No. 62/510,652, filed on May 24, 2017.

(51) Int. Cl.
| *A61M 1/28* | (2006.01) |
| *A61P 7/08* | (2006.01) |
| *A61K 33/14* | (2006.01) |
| *A61K 9/00* | (2006.01) |
| *A61K 9/08* | (2006.01) |
| *A61K 31/7004* | (2006.01) |
| *A61K 31/716* | (2006.01) |
| *A61M 27/00* | (2006.01) |
| *A61M 31/00* | (2006.01) |
| *A61L 2/00* | (2006.01) |

(52) U.S. Cl.
CPC ........... *A61M 1/282* (2014.02); *A61K 9/0019* (2013.01); *A61K 9/08* (2013.01); *A61K 31/7004* (2013.01); *A61K 31/716* (2013.01); *A61K 33/14* (2013.01); *A61M 1/28* (2013.01); *A61M 1/285* (2013.01); *A61M 1/287* (2013.01); *A61M 27/002* (2013.01); *A61M 31/002* (2013.01); *A61P 7/08* (2018.01); *A61L 2/0047* (2013.01); *A61L 2202/21* (2013.01); *A61M 2205/18* (2013.01); *A61M 2205/3317* (2013.01); *A61M 2205/3337* (2013.01); *A61M 2205/3344* (2013.01); *A61M 2205/3368* (2013.01); *A61M 2205/3379* (2013.01); *A61M 2205/3569* (2013.01); *A61M 2205/3576* (2013.01); *A61M 2205/502* (2013.01); *A61M 2205/52* (2013.01); *A61M 2205/587* (2013.01); *A61M 2205/6009* (2013.01); *A61M 2205/70* (2013.01); *A61M 2205/8206* (2013.01); *A61M 2205/8243* (2013.01); *A61M 2209/086* (2013.01); *A61M 2209/088* (2013.01); *A61M 2210/1017* (2013.01); *A61M 2210/1085* (2013.01)

(58) Field of Classification Search
None
See application file for complete search history.

(56) References Cited

U.S. PATENT DOCUMENTS

| 3,233,610 A | 2/1966 | Charles et al. |
| 3,516,410 A | 6/1970 | Hakim et al. |
| 3,540,451 A | 11/1970 | Zeman et al. |
| 3,575,158 A | 4/1971 | Summers |
| 3,608,088 A | 9/1971 | Dorman et al. |
| 3,626,950 A | 12/1971 | Schulte |
| 3,642,004 A | 2/1972 | Osthagen et al. |
| 3,654,932 A | 4/1972 | Newkirk et al. |
| 3,669,116 A | 6/1972 | Heyer |
| 3,810,259 A | 5/1974 | Summers |
| 3,910,283 A | 10/1975 | Leveen |
| 4,014,346 A | 3/1977 | Brownlee et al. |
| 4,083,786 A | 4/1978 | Tsuda et al. |
| 4,240,434 A | 12/1980 | Newkirk |
| 4,261,341 A | 4/1981 | Hakim et al. |
| 4,347,543 A | 8/1982 | Frister et al. |
| 4,354,933 A | 10/1982 | Lester |

(Continued)

FOREIGN PATENT DOCUMENTS

| CN | 101485683 A | 7/2009 |
| CN | 201930383 U | 8/2011 |

(Continued)

OTHER PUBLICATIONS

U.S. Appl. No. 10/369,550 / U.S. Pat. No. 7,335,179, filed Feb. 21, 2003 / Feb. 26, 2008.

(Continued)

Primary Examiner — Robert A Wax
Assistant Examiner — Randeep Singh
(74) Attorney, Agent, or Firm — Eversheds Sutherland (US) LLP; Christopher C. Bolten; Nicola A. Pisano

(57) ABSTRACT

A direct sodium removal ("DSR") infusate regimen and methods of use are provided for removing sodium and reducing fluid overload in patients with severe renal dysfunction and/or heart failure, in which a patient has at least a first DSR session with a first DSR infusate having no or low sodium that is instilled into a patient's peritoneal cavity for a first dwell period to cause sodium and excess fluid to migrate to the patient's peritoneal cavity, and thereafter, the patient may undergo conventional dialysis to rebalance the patient's fluid and sodium levels.

20 Claims, 10 Drawing Sheets

(56) References Cited

U.S. PATENT DOCUMENTS

| | | |
|---|---|---|
| 4,368,737 A | 1/1983 | Ash |
| 4,398,910 A | 8/1983 | Blake et al. |
| 4,416,657 A | 11/1983 | Berglund |
| 4,418,693 A | 12/1983 | LeVeen et al. |
| 4,419,094 A | 12/1983 | Patel |
| 4,465,481 A | 8/1984 | Blake |
| 4,468,219 A | 8/1984 | George et al. |
| 4,475,898 A | 10/1984 | Brodner et al. |
| 4,475,899 A | 10/1984 | Muller |
| 4,490,137 A | 12/1984 | Moukheibir |
| 4,553,956 A | 11/1985 | Muller |
| 4,557,724 A | 12/1985 | Gregonis et al. |
| 4,584,994 A | 4/1986 | Bamberger et al. |
| 4,594,631 A | 6/1986 | Iwaki |
| 4,595,390 A | 6/1986 | Hakim et al. |
| 4,610,625 A | 9/1986 | Bunn |
| 4,610,658 A | 9/1986 | Buchwald et al. |
| 4,615,691 A | 10/1986 | Hakim et al. |
| 4,618,343 A | 10/1986 | Polaschegg |
| 4,632,435 A | 12/1986 | Polyak |
| 4,650,463 A | 3/1987 | LeVeen et al. |
| 4,657,530 A | 4/1987 | Buchwald et al. |
| 4,687,471 A | 8/1987 | Twardowski et al. |
| 4,690,673 A | 9/1987 | Bloomquist |
| 4,725,207 A | 2/1988 | Buchwald et al. |
| 4,772,257 A | 9/1988 | Hakim et al. |
| 4,779,614 A | 10/1988 | Moise |
| 4,784,638 A | 11/1988 | Ghajar et al. |
| 4,850,955 A | 7/1989 | Newkirk |
| D303,840 S | 10/1989 | Weilbacher |
| 4,880,414 A | 11/1989 | Whipple |
| 4,904,236 A | 2/1990 | Redmond et al. |
| 4,950,232 A | 8/1990 | Ruzicka et al. |
| 4,963,129 A | 10/1990 | Rusch |
| 4,963,133 A | 10/1990 | Whipple |
| 4,991,594 A | 2/1991 | Angelchik |
| 5,011,472 A | 4/1991 | Aebischer et al. |
| 5,021,048 A | 6/1991 | Buckholtz |
| 5,037,385 A | 8/1991 | O'Byrne |
| 5,045,057 A | 9/1991 | Van Driessche et al. |
| 5,057,075 A | 10/1991 | Moncrief et al. |
| 5,071,408 A | 12/1991 | Ahmed |
| 5,078,688 A | 1/1992 | Lobodzinski et al. |
| 5,141,493 A | 8/1992 | Jacobsen et al. |
| 5,147,281 A | 9/1992 | Thornton et al. |
| 5,167,615 A | 12/1992 | East et al. |
| 5,180,387 A | 1/1993 | Ghajar et al. |
| 5,254,084 A | 10/1993 | Geary |
| 5,356,386 A | 10/1994 | Goldberg et al. |
| 5,360,414 A | 11/1994 | Yarger |
| 5,385,541 A | 1/1995 | Kirsch et al. |
| 5,387,188 A | 2/1995 | Watson |
| 5,387,192 A | 2/1995 | Glantz et al. |
| 5,391,143 A | 2/1995 | Kensey |
| 5,395,320 A | 3/1995 | Padda et al. |
| 5,395,350 A | 3/1995 | Summers |
| 5,397,354 A | 3/1995 | Wilk et al. |
| 5,431,637 A | 7/1995 | Okada et al. |
| 5,472,323 A | 12/1995 | Hirabayashi et al. |
| 5,474,683 A | 12/1995 | Bryant et al. |
| 5,489,276 A | 2/1996 | Jamshidi |
| 5,520,632 A | 5/1996 | LeVeen et al. |
| 5,549,579 A | 8/1996 | Batdorf et al. |
| 5,575,770 A | 11/1996 | Melsky et al. |
| 5,589,197 A | 12/1996 | Shockley et al. |
| 5,593,394 A | 1/1997 | Kanesaka et al. |
| 5,629,025 A | 5/1997 | Shockley et al. |
| 5,631,025 A | 5/1997 | Shockley et al. |
| 5,637,083 A | 6/1997 | Bertrand et al. |
| 5,676,670 A | 10/1997 | Kim |
| 5,713,864 A | 2/1998 | Verkaart |
| 5,725,506 A | 3/1998 | Freeman et al. |
| 5,788,468 A | 8/1998 | Dewa et al. |
| 5,830,172 A | 11/1998 | LeVeen et al. |
| 5,902,336 A | 5/1999 | Mishkin |
| 5,944,684 A | 8/1999 | Roberts et al. |
| 5,947,911 A | 9/1999 | Wong et al. |
| 5,980,478 A | 11/1999 | Gorsuch et al. |
| 5,980,480 A | 11/1999 | Rubenstein et al. |
| 5,989,207 A | 11/1999 | Hughes |
| 6,007,511 A | 12/1999 | Prywes |
| 6,017,355 A | 1/2000 | Hessel et al. |
| D420,738 S | 2/2000 | Carter et al. |
| 6,022,333 A | 2/2000 | Kensey |
| 6,027,442 A | 2/2000 | Von Iderstein |
| 6,099,513 A | 8/2000 | Spehalski |
| 6,132,405 A | 10/2000 | Nilsson et al. |
| 6,132,415 A | 10/2000 | Finch et al. |
| 6,146,354 A | 11/2000 | Beil |
| 6,162,238 A | 12/2000 | Kaplan et al. |
| 6,162,487 A | 12/2000 | Darouiche |
| 6,193,684 B1 | 2/2001 | Burbank et al. |
| 6,214,802 B1 | 4/2001 | Nakamura et al. |
| 6,245,039 B1 | 6/2001 | Brugger et al. |
| 6,248,726 B1 | 6/2001 | Alsop et al. |
| 6,254,567 B1 | 7/2001 | Treu et al. |
| 6,264,601 B1 | 7/2001 | Jassawalla et al. |
| 6,264,625 B1 | 7/2001 | Rubenstein et al. |
| 6,417,750 B1 | 7/2002 | Sohn |
| 6,436,087 B1 | 8/2002 | Lewis et al. |
| 6,478,789 B1 | 11/2002 | Spehalski et al. |
| 6,533,733 B1 | 3/2003 | Ericson et al. |
| 6,554,822 B1 | 4/2003 | Holschneider et al. |
| 6,585,681 B2 | 7/2003 | Brugger et al. |
| 6,613,095 B1 | 9/2003 | Levin |
| 6,648,906 B2 | 11/2003 | Lasheras et al. |
| 6,656,227 B2 | 12/2003 | Levin |
| 6,689,085 B1 | 2/2004 | Rubenstein et al. |
| 6,814,547 B2 | 11/2004 | Childers et al. |
| 6,827,682 B2 | 12/2004 | Bugge et al. |
| 6,845,267 B2 | 1/2005 | Harrison et al. |
| 6,846,168 B2 | 1/2005 | Davis et al. |
| 6,854,467 B2 | 2/2005 | Boekstegers |
| 6,875,192 B1 | 4/2005 | Saul et al. |
| 6,887,214 B1 | 5/2005 | Levin et al. |
| 6,894,456 B2 | 5/2005 | Tsukamoto et al. |
| 6,905,474 B2 | 6/2005 | Borgesen |
| 6,911,014 B2 | 6/2005 | Wentling et al. |
| 6,921,378 B2 | 7/2005 | O'Keefe et al. |
| 6,926,691 B2 | 8/2005 | Miethke |
| 6,939,111 B2 | 9/2005 | Huitt et al. |
| 6,945,949 B2 | 9/2005 | Wilk |
| 6,949,080 B2 | 9/2005 | Wolf et al. |
| 6,953,481 B2 | 10/2005 | Phelps et al. |
| 6,955,655 B2 | 10/2005 | Burbank et al. |
| 6,960,179 B2 | 11/2005 | Gura |
| 6,964,652 B2 | 11/2005 | Guiles et al. |
| 6,966,889 B2 | 11/2005 | Saab |
| 6,974,445 B2 | 12/2005 | Stergiopulos |
| 6,976,973 B1 | 12/2005 | Ruddell et al. |
| 6,979,351 B2 | 12/2005 | Forsell et al. |
| 6,981,964 B2 | 1/2006 | Rioux et al. |
| 6,986,752 B2 | 1/2006 | McGuckin, Jr. et al. |
| 6,994,700 B2 | 2/2006 | Elkins et al. |
| 7,011,095 B2 | 3/2006 | Wolf et al. |
| 7,017,340 B2 | 3/2006 | Chicky |
| 7,025,739 B2 | 4/2006 | Saul |
| 7,025,742 B2 | 4/2006 | Rubenstein et al. |
| 7,063,679 B2 | 6/2006 | Maguire et al. |
| 7,128,735 B2 | 10/2006 | Weston |
| 7,169,303 B2 | 1/2007 | Sullivan et al. |
| 7,195,608 B2 | 3/2007 | Burnett |
| D558,338 S | 12/2007 | Itoh |
| D558,341 S | 12/2007 | Fujiwara et al. |
| D558,342 S | 12/2007 | Fujiwara et al. |
| 7,311,690 B2 | 12/2007 | Burnett |
| 7,335,179 B2 | 2/2008 | Burnett |
| 7,419,483 B2 | 9/2008 | Shehada |
| 7,621,886 B2 | 11/2009 | Burnett |
| 7,670,332 B2 | 3/2010 | O'Keefe et al. |
| 7,909,790 B2 | 3/2011 | Burnett |
| 8,012,118 B2 | 9/2011 | Curtin et al. |
| 8,202,248 B2 | 6/2012 | Burnett et al. |
| 8,241,239 B2 | 8/2012 | Solomon et al. |

(56) References Cited

U.S. PATENT DOCUMENTS

| | | |
|---|---|---|
| 8,394,048 B2 | 3/2013 | Burnett |
| 8,398,577 B2 | 3/2013 | Burnett |
| 8,517,973 B2 | 8/2013 | Burnett |
| 8,585,635 B2 | 11/2013 | Degen et al. |
| 8,600,517 B2 | 12/2013 | Forsell |
| 8,612,013 B2 | 12/2013 | Forsell |
| 8,641,659 B2 | 2/2014 | Soykan et al. |
| 8,704,484 B2 | 4/2014 | Rosik et al. |
| 8,771,221 B2 | 7/2014 | Burnett |
| 8,882,699 B2 | 11/2014 | Burnett |
| 8,961,448 B2 | 2/2015 | Forsell |
| 8,965,523 B2 | 2/2015 | Forsell |
| 8,992,456 B1 | 3/2015 | Powell |
| 9,039,652 B2 | 5/2015 | Degen et al. |
| 9,138,521 B2 | 9/2015 | Solomon et al. |
| 9,138,523 B2 | 9/2015 | Burnett et al. |
| 9,144,660 B2 | 9/2015 | Degen |
| 9,149,613 B2 | 10/2015 | Degen et al. |
| D743,542 S | 11/2015 | Degen |
| D743,543 S | 11/2015 | Degen |
| 9,339,636 B1 | 5/2016 | Khan et al. |
| 9,381,301 B2 | 7/2016 | Lattanzio et al. |
| 9,421,347 B2 | 8/2016 | Burnett |
| 9,577,459 B2 | 2/2017 | Degen et al. |
| 9,673,527 B2 | 6/2017 | Yoon et al. |
| 9,675,327 B2 | 6/2017 | Johnson et al. |
| 9,694,165 B2 | 7/2017 | Forsell |
| 9,808,634 B2 | 11/2017 | Forsell |
| 9,913,968 B2 | 3/2018 | Burnett |
| 9,956,336 B2 | 5/2018 | Degen et al. |
| 10,252,037 B2 | 4/2019 | Degen et al. |
| 10,398,824 B2 | 9/2019 | Burnett et al. |
| 10,569,003 B2 | 2/2020 | Degen et al. |
| 10,716,922 B2 | 7/2020 | Degen et al. |
| 10,769,244 B2 | 9/2020 | Degen et al. |
| 10,898,631 B2 | 1/2021 | Inhaber et al. |
| 2001/0025170 A1 | 9/2001 | Paderni |
| 2001/0027289 A1 | 10/2001 | Treu et al. |
| 2002/0013545 A1 | 1/2002 | Soltanpour et al. |
| 2002/0022793 A1 | 2/2002 | Bertrand et al. |
| 2002/0091352 A1 | 7/2002 | McGuckin, Jr. et al. |
| 2002/0107467 A1 | 8/2002 | Levin |
| 2002/0123715 A1 | 9/2002 | Sorenson et al. |
| 2003/0114787 A1 | 6/2003 | Gura |
| 2003/0114898 A1 | 6/2003 | Von Arx et al. |
| 2003/0163079 A1 | 8/2003 | Burnett |
| 2003/0171710 A1 | 9/2003 | Bassuk et al. |
| 2003/0217962 A1 | 11/2003 | Childers et al. |
| 2003/0220606 A1 | 11/2003 | Busby et al. |
| 2004/0018228 A1 | 1/2004 | Fischell et al. |
| 2004/0049288 A1 | 3/2004 | Levin |
| 2004/0098113 A1 | 5/2004 | Forsell et al. |
| 2004/0106205 A1 | 6/2004 | Stevenson et al. |
| 2004/0126775 A1 | 7/2004 | Altieri et al. |
| 2004/0147871 A1 | 7/2004 | Burnett |
| 2005/0096582 A1 | 5/2005 | Burnett |
| 2005/0131340 A1 | 6/2005 | Sorenson et al. |
| 2005/0273034 A1 | 12/2005 | Burnett |
| 2006/0010014 A1 | 1/2006 | Brown |
| 2006/0024200 A1 | 2/2006 | Nishikiori et al. |
| 2006/0036208 A1 | 2/2006 | Burnett |
| 2006/0058731 A1 | 3/2006 | Burnett et al. |
| 2006/0094984 A1 | 5/2006 | Wood et al. |
| 2007/0055197 A1 | 3/2007 | Shakir |
| 2007/0106205 A1 | 5/2007 | Connell et al. |
| 2007/0208323 A1 | 9/2007 | Gregorich et al. |
| 2007/0228071 A1 | 10/2007 | Kamen et al. |
| 2007/0233042 A1 | 10/2007 | Moehle et al. |
| 2007/0255345 A1 | 11/2007 | Krause |
| 2007/0299317 A1 | 12/2007 | Hoyme et al. |
| 2008/0024294 A1 | 1/2008 | Mazar |
| 2008/0108935 A1 | 5/2008 | Nyhart |
| 2008/0129486 A1 | 6/2008 | Jeckelmann et al. |
| 2008/0154173 A1 | 6/2008 | Burnett |
| 2008/0214983 A1 | 9/2008 | Mauge et al. |
| 2008/0230450 A1 | 9/2008 | Burbank et al. |
| 2009/0054874 A1 | 2/2009 | Barron et al. |
| 2009/0069642 A1 | 3/2009 | Gao et al. |
| 2009/0171241 A1 | 7/2009 | Garcia et al. |
| 2009/0198174 A1 | 8/2009 | Childers et al. |
| 2009/0222065 A1 | 9/2009 | Dlugos, Jr. et al. |
| 2009/0275805 A1 | 11/2009 | Lane et al. |
| 2009/0275924 A1 | 11/2009 | Lattanzio et al. |
| 2009/0318844 A1 | 12/2009 | Burnett |
| 2010/0010832 A1 | 1/2010 | Boute et al. |
| 2010/0022902 A1 | 1/2010 | Lee et al. |
| 2010/0114012 A1 | 5/2010 | Sandford et al. |
| 2010/0185225 A1 | 7/2010 | Albrecht et al. |
| 2010/0215375 A1 | 8/2010 | Reams |
| 2010/0222846 A1 | 9/2010 | Goetz |
| 2010/0234793 A1 | 9/2010 | Dacey, Jr. et al. |
| 2010/0249692 A1 | 9/2010 | Dacey, Jr. et al. |
| 2010/0270970 A1 | 10/2010 | Toya et al. |
| 2010/0312163 A1 | 12/2010 | Forsell |
| 2010/0312164 A1 | 12/2010 | Forsell |
| 2011/0025261 A1 | 2/2011 | Bersenev |
| 2011/0034986 A1 | 2/2011 | Chou et al. |
| 2011/0163714 A1 | 7/2011 | Ettes et al. |
| 2011/0172545 A1 | 7/2011 | Grudic et al. |
| 2011/0184339 A1 | 7/2011 | Tan |
| 2011/0184340 A1 | 7/2011 | Tan et al. |
| 2011/0202041 A1 | 8/2011 | Forsell |
| 2011/0291613 A1 | 12/2011 | Rosik et al. |
| 2012/0032522 A1 | 2/2012 | Schatz et al. |
| 2012/0035255 A1 | 2/2012 | Fanelli et al. |
| 2012/0041279 A1 | 2/2012 | Freeman et al. |
| 2012/0209085 A1 | 8/2012 | Degen et al. |
| 2012/0209165 A1 | 8/2012 | Degen et al. |
| 2012/0235503 A1 | 9/2012 | Kesler et al. |
| 2012/0235634 A1 | 9/2012 | Hall et al. |
| 2013/0187619 A1 | 7/2013 | Dunipace |
| 2013/0199998 A1 | 8/2013 | Kelly et al. |
| 2013/0211322 A1 | 8/2013 | Degen et al. |
| 2013/0289334 A1 | 10/2013 | Badstibner et al. |
| 2013/0303971 A1 | 11/2013 | Budgett et al. |
| 2013/0317476 A1 | 11/2013 | Searle et al. |
| 2014/0005743 A1 | 1/2014 | Giuffrida et al. |
| 2014/0012180 A1 | 1/2014 | Levin et al. |
| 2014/0066841 A1 | 3/2014 | Degen et al. |
| 2014/0074180 A1 | 3/2014 | Heldman et al. |
| 2014/0098627 A1 | 4/2014 | Mochizuki et al. |
| 2014/0121590 A1 | 5/2014 | Degen |
| 2014/0200481 A1 | 7/2014 | Johnson et al. |
| 2014/0213966 A1 | 7/2014 | Ostapoff et al. |
| 2014/0266022 A1 | 9/2014 | Degen et al. |
| 2014/0275727 A1 | 9/2014 | Bonde et al. |
| 2014/0275827 A1 | 9/2014 | Gill et al. |
| 2015/0088090 A1 | 3/2015 | Macy, Jr. |
| 2016/0000984 A1 | 1/2016 | Burnett et al. |
| 2016/0022971 A1 | 1/2016 | Degen et al. |
| 2016/0087687 A1 | 3/2016 | Kesler et al. |
| 2016/0151553 A1 | 6/2016 | Bonde |
| 2016/0183819 A1 | 6/2016 | Burnett et al. |
| 2016/0303313 A1 | 10/2016 | Burke et al. |
| 2016/0331947 A1 | 11/2016 | Burnett |
| 2017/0079760 A1 | 3/2017 | Newman et al. |
| 2017/0128654 A1 | 5/2017 | Feld |
| 2017/0136221 A1 | 5/2017 | Budgett et al. |
| 2017/0173262 A1 | 6/2017 | Veltz |
| 2017/0281848 A1 | 10/2017 | Axelsson et al. |
| 2017/0304597 A1 | 10/2017 | Forsell |
| 2018/0056050 A1 | 3/2018 | Degen et al. |
| 2018/0060520 A1 | 3/2018 | Degen et al. |
| 2018/0093081 A1 | 4/2018 | Forsell |
| 2018/0243495 A1 | 8/2018 | Degen et al. |
| 2018/0338914 A1 | 11/2018 | Inhaber et al. |
| 2018/0344917 A1 | 12/2018 | Inhaber et al. |
| 2019/0232029 A1 | 8/2019 | Degen et al. |
| 2020/0054813 A1 | 2/2020 | Burnett et al. |

FOREIGN PATENT DOCUMENTS

| | | |
|---|---|---|
| EP | 0366389 A2 | 5/1990 |
| EP | 0980685 A2 | 2/2000 |

(56) References Cited

FOREIGN PATENT DOCUMENTS

| | | | |
|---|---|---|---|
| EP | 1362605 A1 | 11/2003 |
| EP | 1517718 A1 | 3/2005 |
| EP | 1539294 A1 | 6/2005 |
| EP | 1517718 B1 | 10/2010 |
| EP | 2244662 A1 | 11/2010 |
| EP | 2244663 A1 | 11/2010 |
| EP | 2244667 A1 | 11/2010 |
| EP | 2244758 A1 | 11/2010 |
| EP | 2244759 A1 | 11/2010 |
| EP | 2244760 A1 | 11/2010 |
| EP | 1539294 B1 | 1/2011 |
| EP | 2676638 A1 | 12/2013 |
| EP | 2349473 B1 | 12/2016 |
| EP | 2676638 B1 | 7/2017 |
| EP | 3275505 A1 | 1/2018 |
| EP | 2054105 B1 | 7/2018 |
| GB | 2350794 A | 12/2000 |
| JP | S63143074 A | 6/1988 |
| JP | H04327857 A | 11/1992 |
| JP | H0956810 A | 3/1997 |
| JP | 2000072658 A | 3/2000 |
| JP | 2000510552 A | 8/2000 |
| JP | 2004513681 A | 5/2004 |
| JP | 2005171892 A | 6/2005 |
| JP | 2005534400 A | 11/2005 |
| JP | 2006507018 A | 3/2006 |
| JP | 2010527247 A | 8/2010 |
| WO | WO-9741799 A1 | 11/1997 |
| WO | WO-9816171 A1 | 4/1998 |
| WO | WO-9934116 A1 | 7/1999 |
| WO | WO-0207596 A1 | 1/2002 |
| WO | WO-03072166 A1 | 9/2003 |
| WO | WO-2004012806 A1 | 2/2004 |
| WO | WO-2004105730 A1 | 12/2004 |
| WO | WO-2005018708 A2 | 3/2005 |
| WO | WO-2006023589 A2 | 3/2006 |
| WO | WO-2008055248 A2 | 5/2008 |
| WO | WO-2009091267 A2 | 7/2009 |
| WO | WO-2009096854 A1 | 8/2009 |
| WO | WO-2010077851 A2 | 7/2010 |
| WO | WO-2012078230 A1 | 6/2012 |
| WO | WO-2012112664 A1 | 8/2012 |
| WO | WO-2013122580 A1 | 8/2013 |
| WO | WO-2013166038 A2 | 11/2013 |
| WO | WO-2014140277 A1 | 9/2014 |
| WO | WO-2015108782 A1 | 7/2015 |
| WO | WO-2018037359 A1 | 3/2018 |

OTHER PUBLICATIONS

U.S. Appl. No. 10/700,863 / U.S. Pat. No. 7,311,690, filed Nov. 3, 2003 / Dec. 26, 2007.
U.S. Appl. No. 10/826,237 / U.S. Pat. No. 7,909,790, filed Apr. 17, 2004 / Mar. 22, 2011.
U.S. Appl. No. 10/922,478 / U.S. Pat. No. 8,202,248, filed Aug. 18, 2004 / Jun. 19, 2012.
U.S. Appl. No. 11/181,539 / U.S. Pat. No. 7,621,886, filed Jul. 13, 2005 / Nov. 24, 2009.
U.S. Appl. No. 11/198,079 / U.S. Pat. No. 7,195,608, filed Aug. 4, 2005 / Mar. 27, 2007.
U.S. Appl. No. 11/933,214 / U.S. Pat. No. 8,398,577, filed Oct. 31, 2007 / Mar. 19, 2013.
U.S. Appl. No. 12/014,696 / U.S. Pat. No. 8,394,048, filed Jan. 15, 2008 / Mar. 12, 2013.
U.S. Appl. No. 13/029,069 / U.S. Pat. No. 8,517,973, filed Feb. 16, 2011 / Aug. 27, 2013.
U.S. Appl. No. 13/397,498 / U.S. Pat. No. 8,585,635, filed Feb. 15, 2012 / Nov. 19, 2013.
U.S. Appl. No. 13/397,509 / U.S. Pat. No. 9,149,613, filed Feb. 15, 2012 / Oct. 06, 2015.
U.S. Appl. No. 13/397,523 / U.S. Pat. No. 9,039,652, filed Feb. 15, 2012 / May 26, 2015.
U.S. Appl. No. 13/473,516 / U.S. Pat. No. 9,138,523, filed May 16, 2012 / Sep. 22, 2015.
U.S. Appl. No. 13/665,543 / U.S. Pat. No. 9,144,660, filed Oct. 31, 2013 / Sep. 29, 2015.
U.S. Appl. No. 13/789,250 / U.S. Pat. No. 8,771,221, filed Mar. 7, 2013 / Jul. 8, 2014.
U.S. Appl. No. 13/831,642 / U.S. Pat. No. 9,577,459, filed Mar. 15, 2013 / Feb. 21, 2017.
U.S. Appl. No. 13/973,981 / U.S. Pat. No. 8,882,699, filed Aug. 22, 2013 / Nov. 11, 2014.
U.S. Appl. No. 13/973,984 / U.S. Pat. No. 9,421,347, filed Aug. 22, 2013 / Aug. 23, 2016.
U.S. Appl. No. 14/077,005 / U.S. Pat. No. 9,956,336, filed Nov. 11, 2013 / May 1, 2018.
U.S. Appl. No. 14/155,079 / U.S. Pat. No. 9,673,527, filed Jan. 14, 2014 / Jun. 13, 2017.
U.S. Appl. No. 14/856,447 / U.S. Pat. No. 10,398,824, filed Sep. 16, 2015 / Sep. 3, 2019.
U.S. Appl. No. 14/874,187 / U.S. Pat. No. 10,252,037, filed Oct. 2, 2015 / Apr. 9, 2019.
U.S. Appl. No. 15/220,812 / U.S. Pat. No. 9,913,968, filed Jul. 27, 2016 / Mar. 13, 2018.
U.S. Appl. No. 15/249,192 / U.S. Pat. No. 10,716,922, filed Aug. 26, 2016 / Jul. 21, 2020.
U.S. Appl. No. 15/684,479 / U.S. Pat. No. 10,769,244, filed Aug. 23, 2017 / Sep. 8, 2020.
U.S. Appl. No. 15/965,727 / U.S. Pat. No. 10,569,003, filed Apr. 27, 2018 / Feb. 25, 2020.
U.S. Appl. No. 15/985,598 / U.S. Pat. No. 10,918,778, filed May 21, 2018 / Feb. 16, 2021.
U.S. Appl. No. 15/985,617 / U.S. Pat. No. 10,898,631, filed May 21, 2018 / Jan. 26, 2021.
U.S. Appl. No. 16/378,376 / U.S. Pat. No. 11,235,131, filed Apr. 8, 2019 / Feb. 1, 2022.
U.S. Appl. No. 16/550,035, filed Aug. 23, 2019.
U.S. Appl. No. 16/784,106, filed Feb. 6, 2020.
U.S. Appl. No. 17/013,806, filed Sep. 7, 2020.
U.S. Appl. No. 17/174,855, filed Feb. 12, 2021.
U.S. Appl. No. 17/646,858, filed Jan. 3, 2022.
U.S. Appl. No. 17/650,183, filed Feb. 7, 20221.
Adamson et al., "Wireless Pulmonary Artery Pressure Monitoring Guides Management to Reduce Decompensation in Heart Failure With Preserved Ejection Fraction," Circ Heart Fail., 7:935-944 (2014).
Aminde et al., "Current diagnostic and treatment strategies for Lutembacher syndrome: the pivotal role of echocardiography," Cardiovasc Diagn Ther., 5(2):122-132 (2015).
Ando, et al., Left ventricular decompression through a patent foramen ovale in a patient with hypertrophic cardiomyopathy: A case report, Cardiovascular Ultrasound, 2: 1-7 (2004).
Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).
Bellot, et al., Automated Low Flow Pump System for the Treatment of Refractory Ascites: A Multi-Center Safety and Efficacy Study, Journal of Hepatology, 58(5):922-927 (2013).
Benza et al., "Monitoring Pulmonary Arterial Hypertension Using an Implantable Hemodynamic Sensor," Chest, 156(6):1176-1186 (2019).
Ciarka et al., "Atrial Septostomy Decreases Sympathetic Overactivity in Pulmonary Arterial Hypertension," Chest, 131(6):P1831-1837 (2007) (Abstract Only).
Costanzo, et al., Early Ultrafiltration in Patients with Decompensated Heart Failure and Diuretic Resistance, J. Am. Coll. Cardiol., 46(11):2047-2051 (2005).
Davies et al., "Abnormal left heart function after operation for atrial septal defect," British Heart Journal, 32:747-753 (1970).
Doty, et al., Effect of Increased Renal Venous Pressure on Renal Function, J. Trauma., 47(6):1000-1003 (1999).
Extended European Search Report dated May 7, 2021 in EP Patent Appl. Serial No. 20215794.7 (1531).

(56) References Cited

OTHER PUBLICATIONS

Extended European Search Report dated Jun. 6, 2012 in EP Patent Appl. Serial No. EP05786343.3, 6 pages (0330).
Extended European Search Report dated Sep. 18, 2019 in EP Patent Appl. Serial No. 19172235.4 (0831).
Extended European Search Report dated Sep. 14, 2011 in EP Patent Appl. Serial No. EP11172759.0, 6 pages (0231).
Extended European Search Report dated Sep. 26, 2011 in EP Patent Appl. Serial No. EP07844792.7, 6 pages (0730).
Francois, et al., Peritoneal Dialysis for Chronic Congestive Heart Failure, Blood Purif., 40(1):45-52 (2015).
Fukuda, et al., Survivin, a Cancer Target with an Emerging Role in Normal Adult Tissues, Mol. Cancer Ther., 5(5):1087-1098 (2006).
Greitz, et al., Pulsatile Brain Movement and Associated Hydrodynamics Studied by Magnetic Resonance Phase Imaging, Diagnostic Neuroradiology, 34(5): 370-380 (1992).
Hanson, et al., Sodium in the dermis colocates to glycosaminoglycan scaffold, with diminishment in type 2 diabetes mellitus, JCI Insight, 6(12):e145470 (2021).
Hecking, et al., Sodium Setpoint and Sodium Gradient: Influence on Plasma Sodium Change and Weight Gain, Am J. Nephrol, 33(1):39-48 (2011).
Houlberg, et al., Terminal Right Heart Failure Due to Complex Congenital Cardiac Disease Successfully Managed by Home Peritoneal Drainage, Cardiol. Young, 13: 568-570 (2003).
International Search Report & Written Opinion dated Jul. 3, 2012 in Int'l PCT Patent Appl No. PCT/US12/25212, 34 pages (0810).
International Search Report & Written Opinion dated Apr. 15, 2008 in Int'l PCT Patent Appl No. PCT/US07/83261,6 pages (0710).
International Search Report & Written Opinion dated Sep. 28, 2005 in Int'l PCT Patent Appl. No. PCT/US04/26781, 4 pages (0410).
International Search Report & Written Opinion dated Apr. 16, 2015 in Int'l PCT Patent Appl. No. PCT/US2015/010840 (1610).
International Search Report & Written Opinion dated Mar. 18, 2013 in Intl PCT Appl. No. PCT/US2012/025188 (0910).
International Search Report & Written Opinion dated Jan. 4, 2018 in Intl PCT Patent Appl. U.S. Appl. No. PCT/IB2017/055092 (1410).
International Search Report and Written Opinion dated Feb. 2, 2018 in Intl PCT Patent Appl. No. PCT/IB2017/055093 (1710).
International Search Report dated Jul. 17, 2003, PCT/US03/05145, 3 pages (0210).
International Search Report dated Sep. 16, 2008, in Intl PCT Patent Appl. No. PCT/US2005/029305, 4 pages (0310).
Int'l Search Report and Written Opinion dated Aug. 24, 2018 in Int'l PCT Patent Appl. Serial No. PCT/IB2018/053587 (1510).
Kenny., Intra-Abdominal Pressure and Renal Function: the Venous Side of the Road, PulmCCM, Critical Care, Gi and Nutrition, Jul. 14, 2016, accessed on line on Mar. 27, 2017 at http://pulmccm.org/main/2016/critical-care-review/intra-abdominal-pressur-e-renal-function/.
Kulkarni et al., "Lutembacher's syndrome," J Cardiovasc Did Res., 3(2):179-181 (2012).
Kurzyna et al., "Atrial Septostomy in Treatment of End-Stage Right Heart Failure in Patients With Pulmonary Hypertension," Chest, 131:977-983 (2007).
McCausland, et al., Dialysate Sodium, Serum Sodium and Mortality in Maintenance Hemodialysis, 27(4):1613-1618 (2012).
Medtronic Reveal LinqTM LNQ11, Insertable Cardiac Monitor, Clinician Manual, 98 pages (2015).
Munoz, et al., Dialysate Sodium and Sodium Gradient in Maintenance Hemodialysis: a Neglected Sodium Restriction Approach? Nephrol Dial Transplant, 26(4):1281-1287 (2011).
Nakayama, et al., Clinical Effect of Low Na Concentration Dialysate (120mEq/L) for CAPD Patients, Abstracts of the XIII Annual CAPD Conference, Peritoneal Dialysis International, 13(Supplement 1), (1993).
Neragi-Miandoab., Malignant Pleural Effusion, Current and Evolving Approaches for its Diagnosis and Management, Lung Cancer 54:1-9(2006).

Ortiz, et al., Long-Term Automated Peritoneal Dialysis in Patients with Refractory Congestive Heart Failure, Advances in Peritoneal Dialysis, 19:77-80 (2003).
PCT International Search Report and Written Opinion dated Aug. 19, 2014 in PCT Patent Application No. PCT/EP2014/055104 (1310).
Peters et al., "Self-fabricated fenestrated Amplatzer occluders for transcatheter closure of atrial septal defect in patients with left ventricular restriction: midterm results," Clin Res Cardiol., 95:88-92 (2006).
Puttagunta, et al., Peritoneal Dialysis for Heart Failure, Peritoneal Dialysis International, 35(6):645-649 (2015).
Rao, et al., "First-in-Human Experience With Peritoneal Direct Sodium Removal Using A Zero-Sodium Solution," A New Candidate Therapy For Volume Overload, Circulation, vol. 141, 2020, pp. 1043-1053.
Rosenblit, et al., "Peritoneal-Urinary Drainage for Treatment of Refractory Ascites: A Pilot Study," Nov./Dec. 1998, Journal of Vascular and Interventional Radiology, 9(6):998-1005,(1998).
Rosenblum, et al., Conceptual Considerations For Device-Based Therapy in Acute Decompensated Heart Failure, Circulation: Heart Failure, 13(4):e006731 (Apr. 2020).
Ross et al., "Interatrial Communication and Left Atrial Hypertension—A Cause of Continuous Murmur," Circulation, 28:853-860 (1963).
Ruhi, et al., Use of Peritoneal Ultrafiltration in the Elderly Refractory Congestive Heart Failure Patients, Int. Urol. And Nephrol., 44(3):963-969 (2012).
Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).
Schubert, et al., Left ventricular Conditioning in the Elderly Patient to Prevent Congestive Heart Failure After Transcatheter Closure of the Atrial Septal Defect, Catheterization and Cardiovascular Interventions, 64(3): 333-337 (2005).
Second Written Opinion dated May 16, 2019 in Int'l PCT Patent Appl. No. PCT/IB2018/053587 (1510).
Smyth, Chris, Pump implant for Cancer Patients 'is a Game-Changer' for Thousands, the Times, Health News, Jan. 18, 2013 (p. 11).
Sort, et al., Effect of Intravenous Albumin on Renal Impairment and Mortality in Patients with Cirrhosis and Spontaneous Bacterial Peritonitis, The New England Journal of Medicine, 341(6):403-409 (Aug. 5, 1999).
Supplementary European Search Report dated Jun. 4, 2010 in EP Patent Appl. Serial No. EP03719316.6, 3 pages (0230).
Tan et al., The Evidence on the Effectiveness of Management for Malignant Pleural Effusion: A Systematic Review, European Journal of Cardio-thoracic Surgery 29, 2006 (pp. 829-838).
Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).
Toto R.D., "Leveraging the Peritoneal As A New Diuretic Strategy For Heart Failure," Circulation, vol. 141, 2020, pp. 1054-1056.
Viaene et al., "Pulmonary oedema after percutaneous ASD-closure," Acta Cardiol., 65(2):257-260 (2010).
Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).
Warren, et al., Management of Malignant Pleural Effusions Using the Pleurx Catheter, Ann. Thrac. Sur. 85, 2008, (pp. 1049-1055).
Webb et al., "Atrial Septal Defects in the Adult Recent Progress and Overview," Circulation, 114:1645-1653 (2006).
Wiedemann, H.R., "Earliest description by Johann Friedrich Meckel, Senior (1750) of what is known today as Lutembacher syndrome (1916)," Am J Med Genet., 53(1):59-64 (1994) (Abstract Only).

(56) References Cited

OTHER PUBLICATIONS www.medtronic.com/us-en/patients/treatments-therapies/fainting-heart-monit- or/reveal-linq-icm.html (May 2017) (Accessed Nov. 27, 2017).

Zepeda-Orozco, et al., Dialysis Disequilibrium Syndrome, Pediatr. Nephrol, 27:2205-2211 (2012).

Zhang et al., "Acute left ventricular failure after transcatheter closure of a secundum atrial septal defect in a patient with hypertrophic cardiomyopathy," Chin Med J., 124(4):618-621 (2011).

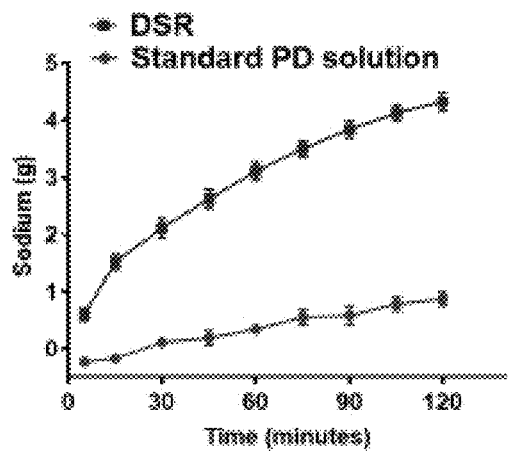
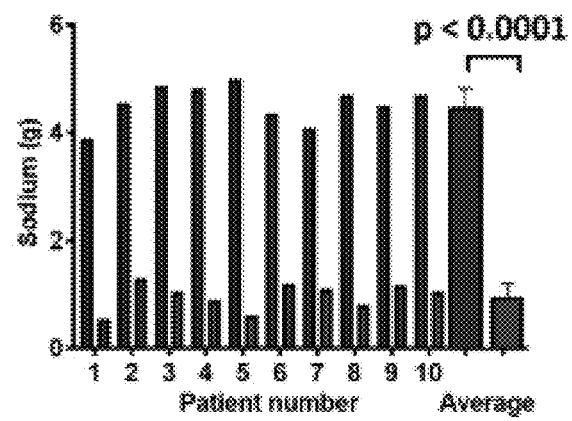
FIG. 8A     FIG. 8B
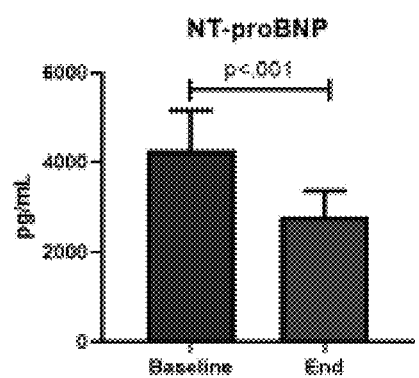
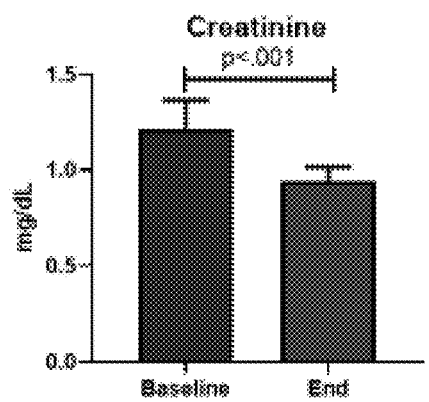
FIG. 9A     FIG. 9B
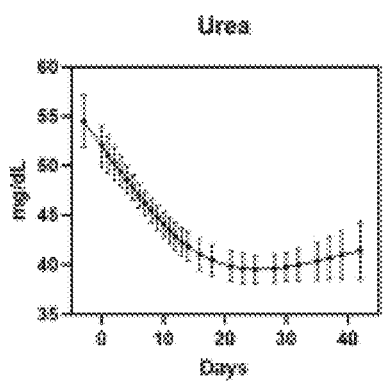
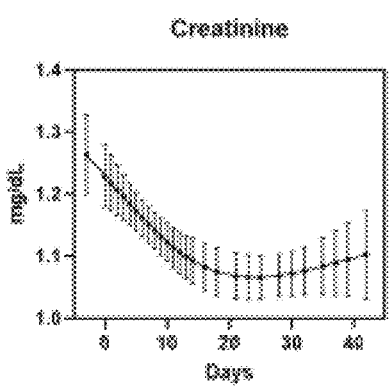
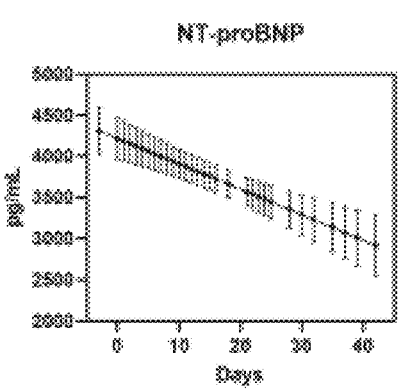
FIG. 10A     FIG. 10 B     FIG. 10C

FORMULATIONS AND METHODS FOR DIRECT SODIUM REMOVAL IN PATIENTS HAVING SEVERE RENAL DYSFUNCTION

CROSS-REFERENCE TO RELATED APPLICATIONS

This application is a continuation-in-part of U.S. patent application Ser. No. 17/174,855, filed Feb. 12, 2021, which is a continuation of U.S. patent application Ser. No. 15/985,598, filed May 21, 2018, now U.S. Pat. No. 10,918,778 B2, which claims the benefit of priority of U.S. Provisional Application Ser. No. 62/510,652, filed May 24, 2017, the entire contents of which are incorporated herein by reference.

FIELD OF THE INVENTION

The present invention relates generally to formulations for, and methods of, using low or sodium-free infusates that are administered to a patient's peritoneal cavity to remove sodium and excess fluid from the body to alleviate fluid overload ("DSR therapy"). U.S. Pat. No. 10,918,778, which is incorporated herein by reference in its entirety, describes such solutions for heart failure patients having residual renal function. The inventions described herein extend DSR therapy to patients with severely compromised renal function.

BACKGROUND

U.S. Pat. No. 10,918,778 B2 describes DSR infusates and methods of use for removing excess fluid by the removal of sodium from heart failure patients having residual renal function. In particular, the DSR infusates are specially formulated to be instilled into a patient's peritoneal cavity to remove sodium and water through one or both of: 1) ultrafiltration and/or 2) diffusion of sodium ions down a steep concentration gradient between the infusate instilled into patient's peritoneal cavity and surrounding tissues and vessels. After sodium and ultrafiltrate accumulates in the peritoneal cavity, it may be drained in accordance with conventional peritoneal dialysis methods, or more preferably, transferred by an implantable pump to the patient's urinary bladder, from which it is subsequently voided.

The foregoing patent describes that excess fluid is eliminated from the body to maintain a relatively stable serum sodium concentration, by one or both of: 1) inducing fluid to migrate from the patient's body into the peritoneal cavity, from where it is eliminated and/or 2) enhancing the excretion of excess fluid via the kidneys through urination. Patients suffering from kidney failure also are prone to accumulate additional sodium in body tissues and suffer from increased fluid retention. Such excess fluid may result in congestive heart failure, which in turn may result in edema of the lungs or liver.

U.S. Pat. No. 5,589,197 to Shockley et al. describes a dialysate for use in peritoneal dialysis, wherein the sodium concentration is between about 35 to 125 meq/L. As discussed in that patent, such solutions may be used to transport sodium to the peritoneal cavity for subsequent removal. Problems encountered with early experience with such low sodium dialysates, included symptomatic drops in blood pressure, and dialysis disequilibrium syndrome, a potentially fatal complication resulting in cerebral edema, coma and death. See, e.g., Nakayma, *Clinical Effect of Low Na Concentration Dialysate (120 mEq/L) for CAPD Patients*, PD Conference, San See, e.g., Zepeda-Orozco D, Quigley R., *Dialysis disequilibrium syndrome*, Pediatric Nephrology (Berlin, Germany) 2012; 27(12):2205-2211.

In accordance with existing standards of care, people with end-stage kidney disease generally undergo dialysis on a regular basis to optimize sodium and fluid levels. The reported current average concentration of sodium in dialysate is generally about 132 mMol/L. See, e.g., Hecking M, Kainz A, Horl W H, Herkner H, Sunder-Plassmann G., *Sodium setpoint and sodium gradient: influence on plasma sodium change and weight gain*. American Journal of Nephrology 2011; 33(1):39-48; Mc Causland F R, Brunelli S M, Waikar S S., *Dialysate sodium, serum sodium and mortality in maintenance hemodialysis*. Nephrology Dialysis Transplantation 2012; 27(4):1613-8.

As reported in, e.g., Munoz Mendoza J, Sun S, Chertow G, Moran J, Doss S, Schiller B., *Dialysate sodium and sodium gradient in maintenance hemodialysis: a neglected sodium restriction approach?*, Nephrology Dialysis Transplantation 2011; 26(4):1281-7, experience with dialysate sodium concentrations higher than the patients' blood sodium levels show that such dialysates generally result in a net gain of sodium by the end of a dialysis session, which may result in increased fluid consumption and hypertension. Consequently, patients who undergo frequent hemodialysis sessions may experience chronic high sodium and fluid retention.

As described in the above-incorporated patent, applicants have observed that eliminating fluid overload is a key clinical objective in managing heart failure. Applicants observed that achieving a stable reduction in fluid retention requires elimination of sodium from the body. Within certain ranges, patients having residual kidney function automatically will rebalance blood serum sodium concentration to maintain a constant serum osmolality and to maintain a stable sodium level, as described for example, in Guyton & Hall, Textbook of Medical Physiology. This is so because in patients with residual kidney function, the kidneys will remove excess water beyond that which might lead to hyponatremia.

As described in the above-incorporated patent, the use of no or low sodium dialysates to reduce fluid and/or sodium overload was believed by applicants to require at least some residual kidney function to avoid undesirable drops in blood pressure caused by hyponatremia and/or dialysis disequilibrium syndrome. It therefore would be desirable to develop DSR formulations and methods of use for conducting DSR therapy for patients with severe renal dysfunction. The desired DSR formulations and methods would assist such patients to achieve reductions in sodium and fluid overload not currently attainable with conventional dialysis techniques, while maintaining sodium serum levels for such patients.

Accordingly, it would be desirable to provide compositions, and methods of use, for expanding the benefits of DSR therapy to patients suffering from severe renal dysfunction.

SUMMARY OF THE INVENTION

In accordance with the present invention, DSR infusates and methods of use are provided for removing sodium and reducing fluid overload in patients with severe renal dysfunction, while aiding maintenance of stable serum sodium levels. In the context of this invention, such patient groups include patients who exhibit chronic kidney disease ("CKD") of Stage 4 or Stage 5, and who in addition to kidney disease also may manifest with any of several forms of heart failure treatable by body fluid management.

Applicants have observed that instilling low or no sodium infusates into the peritoneal cavities of patients with residual renal function can significantly alleviate the symptoms of heart failure by reducing fluid overload. For example, in applicants' first-in-human testing, DSR formulations that comprise a sterile solution of dextrose in a range of 5 to 15 weight percent, with no or low sodium concentrations, resulted in removal of significant amounts of sodium (e.g., up to 2 gm) and fluid (e.g., up to 2 liter) during a two-hour dwell time. Applicants observed that those patients' blood serum sodium levels remained substantially constant. To the extent that the amount of sodium migrating to the patient's peritoneal cavity causes a transitory serum sodium imbalance, the patients' kidneys caused additional water to be excreted to rebalance the blood serum sodium level. Applicants theorize that if sodium migrates to, and is removed from, the peritoneal cavity, serum sodium levels will be maintained by release into the blood of sodium stored in extravascularly, e.g., within the interstitium of skin and skeletal muscle.

For patients with severe renal disease, e.g., CKD stage 4 of stage 5, there is a potential risk that removal of too much sodium via a single peritoneal dialysis session using the DSR infusates described in the above-incorporated patent may (without a corresponding reduction in fluid), may result in hyponatremia. This situation may arise because patients with severe renal dysfunction may be unable to remove excess amounts of water from the blood to maintain a stable serum sodium level. To meet the needs of this patient population, special DSR infusates and methods are needed.

The amount of sodium and water removed during a specified dwell period will be function of the concentration of sodium in the infusate, the osmolality of the infusate, and the tendency of constituents of the infusate to migrate across through the peritoneum and into the patient's tissue and vascular system. For example, an infusate with no sodium will create a steep gradient that causes sodium to migrate to the peritoneal cavity, whereas an infusate with a sodium concentration approaching isomolar with blood serum levels, e.g., 130 meq/ml, will create a much shallower gradient. Sodium will move to the fluid in the peritoneal cavity asymptotically until that gradient disappears and the sodium concentration in the fluid in the peritoneal cavity becomes isotonic, provided the dwell period is sufficiently long.

Similarly, the osmolality of the infusate will determine its ability to drive water to the peritoneal cavity, and will vary based on the constituent in the infusate and its ability to migrate across the peritoneum. For example, it is known that dextrose provides high osmolality when a dextrose containing infusate is instilled into the peritoneal cavity. However, because the dextrose molecules to quickly migrate from the peritoneal cavity, the ability of the infusate to drive ultrafiltrate to the peritoneal cavity will decline fairly rapidly. By comparison, an icodextrin solution also provides high initial osmolality, remains high throughout the dwell period because the icodextrin molecules are less prone to migrate. Accordingly, the ability of the infusate to drive excess fluid into the patient's peritoneal cavity also will determine the ability of the DSR infusate to move excess sodium and water to the peritoneal cavity for subsequent removal. In addition, the more water that is drawn to the peritoneal cavity, the greater the amount of sodium that will migrate to the peritoneal cavity to render the sodium concentration isotonic.

In accordance with one aspect of the present invention, a regimen of DSR infusates having different compositions may be provided for sequential use with patients having severe renal dysfunction. A first infusate composition, may have a first selected no or low sodium concentration, and may be instilled into a patient's peritoneal cavity in an amount from 0.25 L to 1.5 L or more to initiate DSR treatment to reduce fluid and sodium overload to establish a new fluid and sodium equilibrium for the patient. Thereafter, a second infusate composition, having a different composition, may be instilled in an amount of 0.25 L to 2.0 L to remove additional amounts of fluid and sodium to establish a new fluid equilibrium for the patient. Treatment with these solutions may be serial, or coordinated, and/or interspersed, with the patient's conventional hemodialysis or peritoneal dialysis regime.

After a first DSR therapy session, the patient may undergo one or more conventional hemodialysis or peritoneal dialysis sessions to remove blood-borne toxins. For example, a patient may undergo a first DSR therapy session to reduce fluid overload, and thereafter follow-up the DSR therapy session with conventional hemodialysis or peritoneal dialysis treatment to restore any fluid/sodium imbalance. During the first DSR therapy session, an exemplary first DSR infusate may comprise a no or low sodium solution, preferably consisting of sterile water containing 5 weight percent dextrose and up to 40 weight percent icodextrin. In particular, a higher concentration of icodextrin is expected to be desirable to avoid hyperglycemia.

Subsequently, the patient may undergo a second DSR therapy session, during which additional sodium and/or excess fluid may be removed, but in different proportions than during the first therapy session. One exemplary composition for use as a second DSR infusate may comprise a no or low sodium solution consisting of sterile water containing 5 weight percent dextrose and 15 weight percent icodextrin. More generally, during the subsequent DSR therapy session, which may be temporally contiguous with the first session, any of a range of infusates having different dextrose and icodextrin concentrations of between about 5 weight percent and 40 weight percent may be used to target remove of fluid or enhanced sodium depuration as indicated on a patient-specific basis. Optionally, during the dwell period for such a second infusate, serum sodium concentration may be sampled, e.g., via blood samples, to confirm that the serum sodium level does not drop precipitously. A conventional hemodialysis or peritoneal dialysis session may be conducted between the first and second DSR sessions, or shortly thereafter, to further rebalance and stabilize the patient's serum sodium and fluid levels.

Methods of instilling and removing the DSR infusates of the present invention also are provided. In particular, the DSR infusates may be instilled into, and ultrafiltrate removed from, the peritoneal cavity using conventional peritoneal dialysis tubing sets. More preferably, removal of dialysate solution and sodium-laden ultrafiltrate may be accomplished with the implantable pump system described in commonly-assigned U.S. Pat. No. 9,956,336, the contents of which are incorporated herein by reference. That patent describes a system for ambulatory peritoneal dialysis in which a dialysate is infused into the peritoneal cavity. After a predetermined time and/or at predetermined intervals, an implantable pump transfers fluid accumulated in the peritoneum to the patient's bladder, where it may be excreted by urination.

BRIEF DESCRIPTION OF THE DRAWINGS

Further features of the invention, its nature and various advantages will be more apparent from the accompanying drawings and the following detailed description of the preferred embodiments, in which:

FIGS. 8A and 8B are, respectively, graphs showing the amounts of sodium removed in a first in-human ("FIM") trial for 10 patients using a single dose of sodium-free 10 weight percent dextrose solution and a conventional peritoneal dialysis solution, sequentially administered via a conventional peritoneal dialysis catheter, as a function of dwell time, and sodium removal comparisons for each patient.

FIGS. 9A and 9B are, respectively, bar charts that compare average observed changes in physiologic parameters for 10 other human patients during a second trial in which patients underwent DSR sessions three times a week for six weeks with a DSR solution of sodium-free 10 weight percent dextrose solution.

FIGS. 10A, 10B and 10C are, respectively, graphs showing the evolution of observed changes in physiologic parameters for the 10 patients during the second human trial.

DETAILED DESCRIPTION OF THE INVENTION

Figure 1:
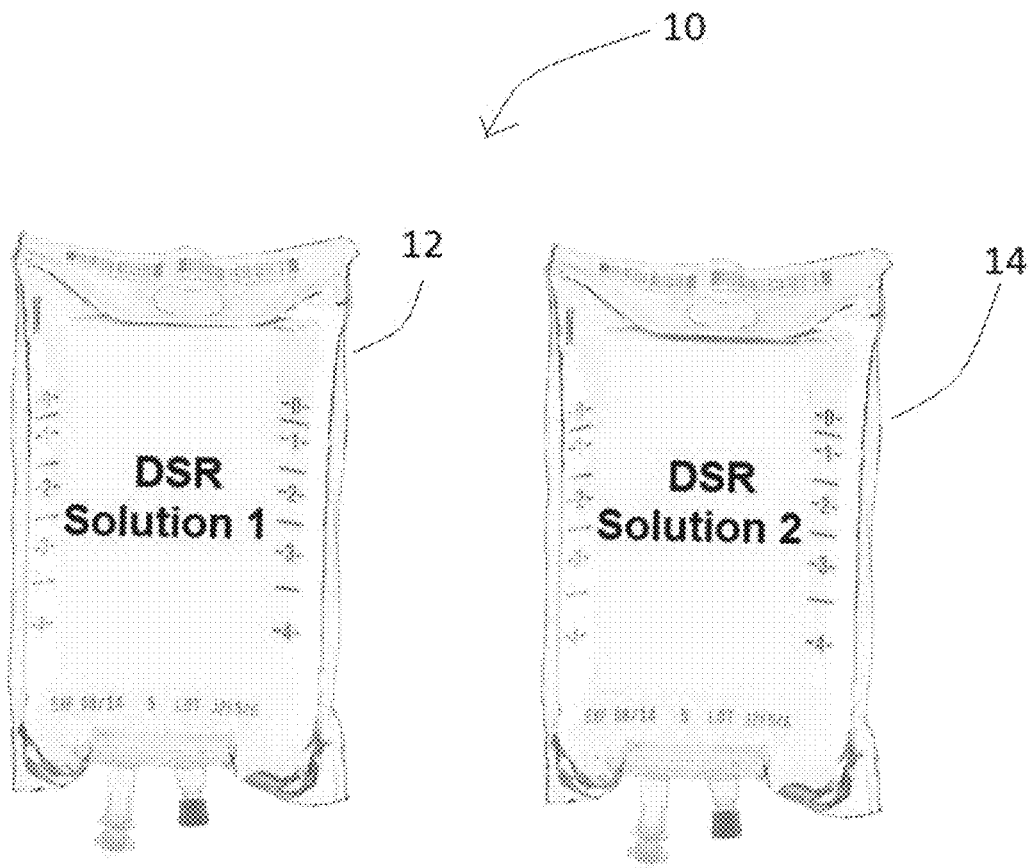
FIG. 1 is a perspective view of an exemplary regimen of infusates having compositions selected in accordance with the principles of the present invention for reducing fluid and sodium overload in patients with severe renal dysfunction.
Figure 1:
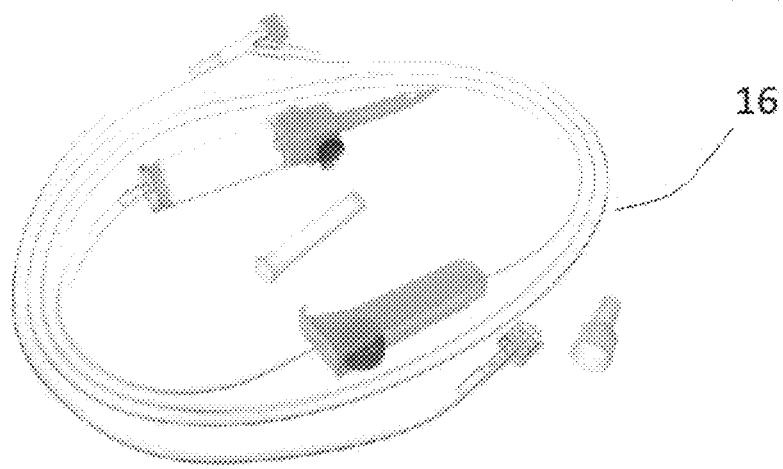

The present invention is directed to infusate compositions and methods of treating fluid and/or sodium overload in patients with severe renal dysfunction, e.g., CKD stage 4 or stage 5. The infusate compositions and treatment methods are expected to be complimentary to conventional hemodialysis or peritoneal dialysis treatments and methods. Methods and compositions for treating heart failure patients suffering from fluid overload that have residual renal function are described in U.S. Pat. No. 10,918,778 B2, which is incorporated herein by reference in its entirety. The present invention is directed to methods and compositions that extend the benefits of direct sodium removal technology to patients with severe renal dysfunction. Based on data collected during first-in-man trials with an exemplary DSR infusate as described in the above-incorporated patent, the methods and compositions of the present invention are expected not only to improve sodium/fluid balance, but also to improve renal function and efficacy of loop diuretics used to control fluid overload.

In accordance with the principles of the present invention, a regimen consisting of at least a first DSR infusate composition is provided having a selected osmolality and no or low sodium. By way of non-limiting example, the first infusate may comprise sterile water, up to 40 wt % icodextrin, and up to 10 wt % dextrose. The regimen also may include a second infusate composition having the same or different composition and sodium concentration. An exemplary second infusate, which may be used in a follow-up DSR session, may comprise sterile water, 15 wt % icodextrin, and 5 wt % dextrose. Other DSR infusates may omit dextrose entirely and consist solely of a low-sodium icodextrin concentration, or have as constituents other high molecule weight biocompatible polymers.

In one embodiment, the first infusate may be constituted so that when instilled into a patient's peritoneal cavity, it creates gradients that cause both high amounts of water and sodium to migrate to infusate during a first dwell period. Upon conclusion of the first dwell period, or a portion thereof, the infusate, ultrafiltrate and sodium are removed from the peritoneal cavity using a conventional peritoneal drainage catheter, or more preferably, an implanted pump that transfers the fluid to the patient's bladder.

A second infusate for use in a subsequent DSR treatment, immediately after or sometime after the first DSR treatment, may be constituted so that when instilled into the patient's peritoneal cavity, it creates gradients that cause additional water and/or sodium to migrate to the peritoneal cavity during a second dwell period. Upon conclusion of the second dwell period, or a portion thereof, the second infusate, ultrafiltrate and sodium may be removed from the peritoneal cavity using a conventional drainage catheter or an implanted pump. The osmolality, constituents and sodium concentration of the second infusate may be adjusted as required on a patient-specific basis to tailor relief desired for that patient.

As described in detail below, for patients with severe renal dysfunction, the DSR infusate regimen is designed to be used in coordination with a patient's regular hemodialysis or peritoneal dialysis schedule. Conventional dialysis treatments, both hemodialysis and peritoneal dialysis, target removal of blood-borne toxins and waste by-products. While conventional dialysis techniques can remove some excess water from the patient's circulation, it is not uncommon for patients with severe renal dysfunction to suffer from fluid overload. In accordance with the principles of the present invention, however, DSR therapy may be used in combination with conventional dialysis techniques to remove sodium, resolve fluid overload, and reduce congestion. Initial FIM results also suggest that DSR therapy may restore some degree of kidney function, improve the efficacy of loop diuretics and mitigate some degree of transient dialysis-induced kidney injury.

As described in the above-incorporated patent, a zero or low sodium concentration in each infusate causes sodium and fluid (osmotic ultrafiltrate) to pass from the patient's body into the peritoneal cavity. The DSR infusate is allowed to remain, or dwell, in the peritoneal cavity for a specified period before it is removed, together with the extracted sodium and the osmotic ultrafiltrate. Removal of the sodium-laden DSR infusate and osmotic ultrafiltrate from the peritoneal cavity may be performed using an implantable system, such as the Alfapump commercialized by Sequana Medical NV of Zwijnaarde, Belgium.

As used in this disclosure, a no or low sodium DSR infusate has a sodium content of less than 120 meq/L, and more preferably, less than 35 meq/L, and includes infusates having zero or only trace amounts of sodium. The fluid overload treatment methods of the present invention specifically contemplate use of the inventive methods in patients experiencing severe kidney dysfunction, e.g., CKD Stage 4 or Stage 5, function and also in heart failure patients with end-stage renal disease.

Referring to FIG. 1, in accordance with the principles and methods of the present invention, an exemplary regimen 10 of DSR infusates suitable for use with patients with severe renal dysfunction is described, and includes two formulations designed to be instilled into a patient's peritoneal cavity having different osmolalities, intended for successive DSR sessions. Specifically, FIG. 1 depicts bag 12 of DSR Solution 1, which may be employed in a first treatment session, and bag 14 of DSR Solution 2, which may be used in a follow-up DSR session as described below. It should be understood, however, that DSR Solution 1 and Solution 2 may consist of a single composition of DSR infusate. Also depicted in FIG. 1 is conventional tubing set 16 for use in infusing the fluid of either bag 12 or 14 into the peritoneal cavity of a patient using a conventional peritoneal dialysis catheter (not shown).

In one embodiment, DSR Solution 1 and DSR Solution 2 are infusates that may have different compositions and are intended for sequential use in patients having severe renal dysfunction. Preferably, such patients regularly undergo conventional hemodialysis or peritoneal dialysis. DSR Solution 1 may have a sodium concentration and osmolality selected for initiating DSR treatment, to reduce fluid and sodium overload. DSR Solution 2 may have a different sodium concentration and osmolality, and may be used in a subsequent DSR session to further reduce fluid and sodium levels achieved with the first DSR session. It expected that one or more DSR sessions may be coordinated, and/or interspersed, with the patient's conventional hemodialysis or peritoneal dialysis regime.

In one method of the invention, after a first DSR therapy session with the DSR Solution 1, the patient may undergo one or more conventional hemodialysis or peritoneal dialysis sessions to remove blood-borne toxins. Thereafter, the patient may undergo a subsequent session using DSR Solution 2 to further reduce fluid and/or stored sodium, or to maintain the fluid/sodium balance achieved after the session with DSR Solution 1.

In one exemplary embodiment of DSR therapy regimen 10, DSR Solution 1 may comprise a no or low sodium solution consisting of sterile water containing 5 to 10 weight percent dextrose and up to 40 weight percent icodextrin. Such an exemplary composition of DSR Solution 1 is expected to remove both sodium and water. Thereafter, the patient may undergo a further DSR therapy session with DSR Solution 2, such that the composition of DSR Solution 2 is selected either to remove additional fluid and/or sodium or to maintain a new fluid/sodium balance achieved after the first DSR session. An exemplary composition for DSR Solution 2 may comprise a no or low sodium solution consisting of sterile water containing 5 weight percent dextrose and 15 weight percent icodextrin. Such an exemplary composition of DSR Solution 2 is expected preferentially to remove more sodium than water, relative to DSR Solution 1.

In accordance with one aspect of the invention, serum sodium concentration may be periodically sampled, e.g., via blood samples, to monitor the patient's serum sodium level. Conventional hemodialysis or peritoneal dialysis sessions may be conducted after or between the first and any second DSR sessions, as generally required for patients with severe renal dysfunction. Advantageously, it is expected that such conventional hemodialysis or peritoneal dialysis sessions also may be used to fine-tune and/or stabilize the patient's fluid management.

Generally, formulations suitable for first and follow-up DSR sessions may contain from zero to 50 grams of dextrose per 100 ml of aqueous solution, and for some applications 5 to 10 weight percent dextrose; from 0.5 to 50 grams of icodextrin per 100 ml of aqueous solution and more preferably 15 to 30 weight percent icodextrin. Suitable solutions also may employ high molecular weight biocompatible polymer solutions (weight average molecular weight Da>10,000) having from 0.5 to 50 grams of high molecular weight polymer per 100 ml of aqueous solution, and combinations thereof. Additional constituents that may be substituted for the dextrose and/icodextrin include solutions containing between 0.5 and 50 grams of one or more of: xylitol, glycerol, hyperbranched polyglycerol, sorbitol, carnitine, taurine, amino acids, urea, polyacrylate, polyethyleneimine, and stevioside per 100 ml aqueous solution. The aqueous solution contains at least purified water, and in addition may include electrolytes such as low amounts of magnesium or calcium salts, preservatives, ingredients having antimicrobial or antifungal properties, or buffering materials to control pH of the infusate. Icodextrin compositions generally may be preferable to dextrose compositions as icodextrin has been observed to experience a lower rate of uptake when employed in a peritoneal dialysis setting, and thus better preserves the peritoneal membrane compared to dextrose-based compositions.

Whereas the DSR infusates described in the U.S. Pat. No. 10,918,778 B2 were not recommended for use in heart failure patients with fluid overload having severe renal dysfunction, the regimen of infusates described herein may be specifically formulated to treat patients with CKD Stage 4 or Stage 5, especially patients for whom loop diuretics are no longer effective. As discussed below, the assignee's initial human testing with a no sodium dextrose solution suggests that interspersing DSR therapy sessions with conventional hemodialysis or peritoneal dialysis sessions enables the latter sessions advantageously to be used to monitor and/or adjust fluid and sodium levels. Those initial studies also revealed that removal of excess fluid and sodium via DSR sessions enabled the use of lower doses of loop diuretics to maintain an appropriate fluid balance for the patient. For some patients loop diuretics could be completely discontinued during the study period. It is theorized that in such cases the DSR therapy permitted the patients' kidneys to rest and/or regain some function, thus enhancing the efficacy of the loop diuretics.

The methods of present invention for using the DSR compositions of the invention optionally may include monitoring a patient's blood serum sodium level in connection with the DSR sessions. For example, a blood sample may be taken during or after DSR session to monitor serum sodium level. Depending upon a desired outcome for a specific patient, use a first DSR infusate may cause more sodium than water to migrate to the patient's peritoneal cavity, which ultrafiltrate together with the infusate and sodium, may be drained from the peritoneal cavity via a conventional peritoneal dialysis catheter or more preferably, using the implantable pump described in the above-incorporated patent. Thereafter, the patient may undergo conventional hemodialysis or peritoneal dialysis, during which additional fluid may be removed to rebalance the patient's sodium metabolism.

At some later time, e.g., several weeks later, after one or several regularly scheduled dialysis sessions, the patient may undergo another DSR session with DSR Solution 1 or DSR Solution 2. Once again the patient's serum sodium level may be monitored by taking a blood sample during or after the DSR session. In accordance with one aspect of the invention, DSR session may be intended to additional water and/or sodium to migrate to the patient's peritoneal cavity. It has been theorized that, as observed during initial testing, the body may store excess sodium in extravascular spaces, such as interstitially in the vessel walls. It is believed that when sodium migrates from the blood and into infusate instilled in the peritoneal cavity during a DSR dwell period, the sodium migrating to the infusate is replenished by the non-osmotic sodium. Accordingly, it is theorized that by reducing non-osmotic sodium, the patient's body will be able to achieve a lower and healthier fluid balance.

While the methods and DSR regimes of the present invention may be performed with conventional peritoneal infusion and drainage catheters, it is expected that use the implantable pump system offered by the assignee of the present application may be particularly advantageous. Specifically, the Alfapump system, offered by Sequana Medical NV, is well suited for removing sodium-laden infusate and ultrafiltrate from a patient's peritoneal cavity. For example, after a DSR infusate is instilled into a patient's peritoneal cavity and a desired dwell time elapses, or a sodium concentration is detected in the ultrafiltrate, the implantable pump may be activated, in accordance with a clinician's programmed instructions, to pump the sodium-laden DSR infusate and ultrafiltrate to the patient's bladder for subsequent voiding. Further, it is possible that after a DSR session, fluid may continue to accumulate in the peritoneal cavity, and the implantable pump may be programmed to pump such fluid to the bladder on a periodic basis.

The methods of the present invention therefore provide a method of controlling fluid overload and edema in patients with severe renal dysfunction, while permitting such patients to experience a more normal lifestyle, other than their regularly scheduled dialysis sessions. And because the inventive methods and compositions are expected to lead to a reduction in fluid and/or sodium volume, the patient may not only experience improved comfort and lifestyle, but also delayed onset of other co-morbidities, such as further advancement of chronic kidney disease and/or progressive heart failure.

Figure 2:
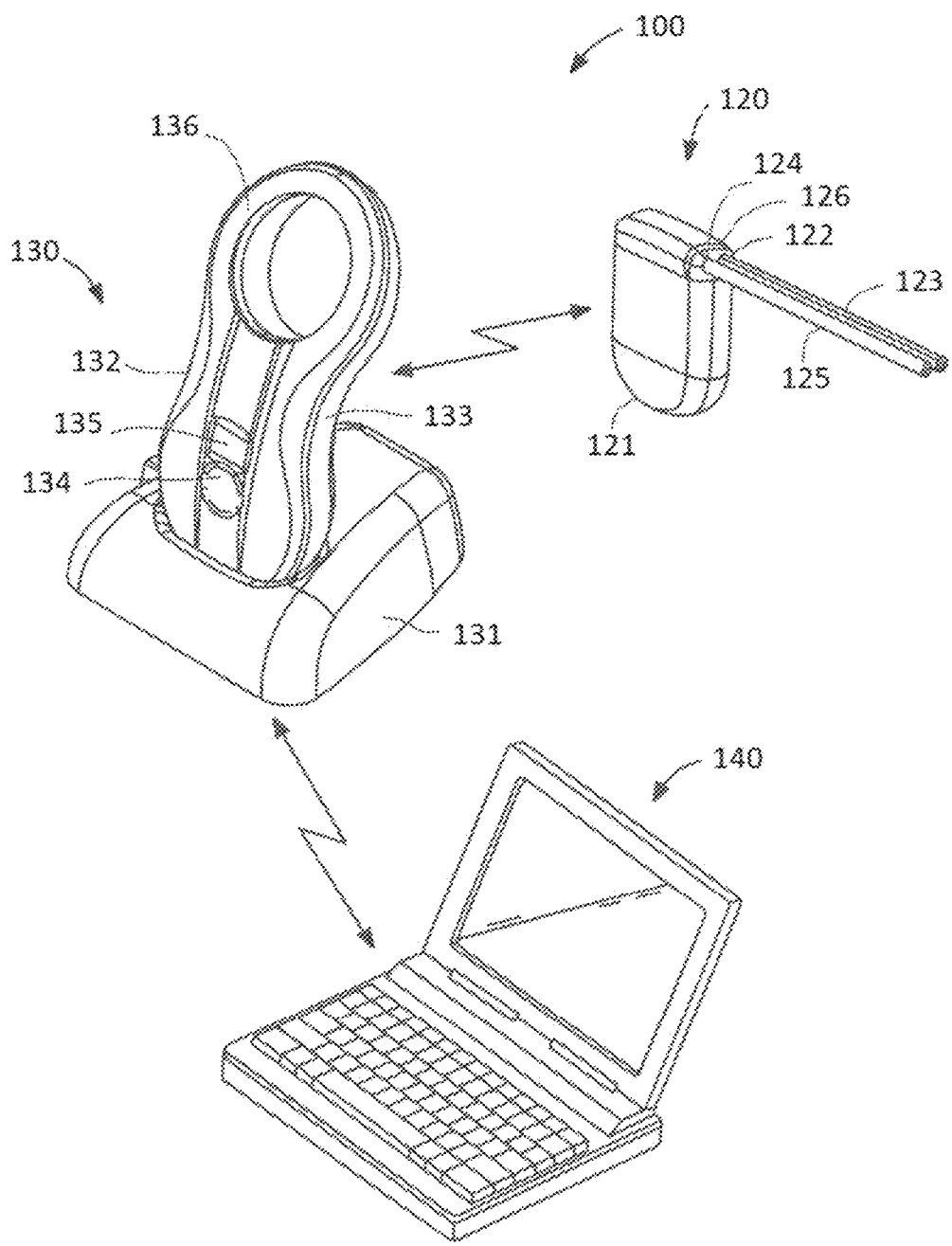
FIG. 2 is a plan view of exemplary components of an implantable pump system for use in conjunction with the infusate compositions and methods of the present invention.

Referring now to FIG. 2, exemplary system 100 for use in practicing the present invention is described. In FIG. 2, components of system 100 are not depicted to scale on either a relative or absolute basis. System 100 includes implantable pump 120 that is specially configured to move fluid out of the peritoneal cavity and into the bladder, and includes a plurality of sensors for monitoring and recording operating parameters relevant to the health of the patient. External charging and communication system 130 is used to periodically charge and communicate with implantable device 110, and downloads operational data from device 110. Monitoring and control system 140 includes software installed on a treating physician's computer to receive the operational data from charging and communication system 130, and allow the physician to modify the operation of implantable device 110 based on the physician's perception of the patient's health based on review of the operational data uploaded from device 110. Optionally, the monitoring and control system may be configured to alert the physician as to a prediction or detection of infection, heart failure decompensation or other clinical events based on the recorded operating parameters. Implantable device 110 optionally may also include one or more ultraviolet (UV) sources configured to inhibit infection.

During patient visits, charging and communication system 130 may be coupled, either wirelessly or using a cable, to monitoring and control system 140 to download for review data stored on implantable device 120, or to adjust the operational parameters of the implantable device. Monitoring and control system 140 also may be configured to upload and store date retrieved from charging and communication system 130 to a remote server (not shown) for later access by the physician or charging and communications system 130.

Implantable device 120 comprises an electromechanical pump having housing 121 configured for subcutaneous implantation. Implantable device 120 preferably includes an electrically-driven mechanical gear pump having connectors 122 and 124. Bladder catheter 125 is coupled to pump housing 121 via connector 124. Peritoneal catheter 123 is coupled to pump housing 121 via connector 122. Peritoneal catheter 123 comprises a tube having a first (proximal) end configured to be coupled to pump housing 121 and a second (distal) end configured to be positioned in the peritoneal cavity. Bladder catheter 125 comprises a tube having a first (proximal) end configured to be coupled to pump housing 121 and a second (distal) end configured to be inserted through the wall of, and fixed within, a patient's bladder. In a preferred embodiment, both catheters are made of medical-grade silicone and include polyester cuffs at their distal ends (not shown) to maintain the catheters in position.

Implantable device 120 also may include pressure sensors that monitor pressure in one or both of the peritoneal cavity and the bladder, such that fluid is pumped from the peritoneal cavity to the bladder if the intra-abdominal pressure exceeds a limit determined by the physician. Alternatively, or in addition, the output of the pressure sensors may interrupt pumping of fluid to the bladder until the bladder is determined to have sufficient space to accommodate additional fluid. For patient comfort, implantable device 120 optionally may be programmed not to pump at night or when an accelerometer included in the implantable device indicates that the patient is asleep (and thus unlikely to be able to void the bladder). Implantable device 120 preferably includes multiple separate fail-safe mechanisms, to ensure that urine cannot pass from the bladder to the peritoneal cavity through the pump, thereby reducing the risk of transmitting infection.

External charging and communication system 130, in a preferred form, includes base 131 and handpiece 132. In this embodiment, handpiece 132 contains a controller, a radio transceiver, an inductive charging circuit, a battery, a quality-of-charging indicator and a display, and is removably coupled to base 131 to recharge its battery. Base 131 may contain a transformer and circuitry for converting conventional 120V or 220-240V service to a suitable DC current to charge handpiece 132 when coupled to base 131. In alternative embodiments, handpiece 132 may include such circuitry and a detachable power cord, thereby permitting the handpiece to be directly plugged into a wall socket to charge the battery. In a preferred embodiment, each of implantable device 120 and handpiece 132 includes a device identifier stored in memory, such that handpiece 132 provided to the patient is coded to operate only with that patient's specific implantable device 120.

Handpiece 132 preferably includes housing 133 having multi-function button 134, display 135, a plurality of light emitting diodes (LEDs, not shown) and inductive coil portion 136. Multi-function button 134 provides the patient the ability to issue a limited number of commands to implantable device 120, while display 135 provides visible confirmation that a desired command has been input; it also displays battery status. Inductive coil portion 136 houses an inductive coil that is used transfer energy from handpiece 132 to recharge the battery of implantable device 120. The LEDs, which are visible through the material of housing 133 when lit, may be arranged in three rows of two LEDs each, and are coupled to the control circuitry and inductive charging circuit contained within handpiece 132. The LEDs may be arranged to light up to reflect the degree of inductive coupling achieved between handpiece 132 and implantable device 120 during recharging of the latter. Alternatively, the LEDs may be omitted and an analog display provided on display 135 indicating the quality of inductive coupling.

Control circuitry contained within handpiece 132 is coupled to the inductive charging circuit, battery, LEDs and radio transceiver, and includes memory for storing information from implantable device 120. Handpiece 132 also preferably includes a data port, such as a USB port, that permits the handpiece to be coupled to monitoring and control system 140 during visits by the patient to the physician's office. Alternatively, handpiece 132 may include a wireless chip, e.g., conforming to the Bluetooth or IEEE 802.11 wireless standards, thereby enabling the handpiece to communicate wirelessly with monitoring and control system 140, either directly or via the Internet.

Monitoring and control system 140 is intended primarily for use by the physician and comprises software configured to run on a conventional computer, e.g., a laptop as illustrated in FIG. 2 or tablet or smartphone. The software enables the physician to configure, monitor and control operation of charging and communication system 130 and implantable device 120. The software may include routines for configuring and controlling pump operation, such as a target amount of fluid to move daily or per motor actuation, intervals between pump actuation, and limits on peritoneal cavity pressure, bladder pressure, pump pressure, and battery temperature. System 140 also may provide instructions to implantable device 120 via charging and control system 130 to control operation of implantable device 120 so as not to move fluid during specific periods (e.g., at night) or to defer pump actuation if the patient is asleep.

System 140 further may be configured, for example, to send immediate commands to the implantable device to start or stop the pump, or to operate the pump in reverse or at high power to unblock the pump or associated catheters. The software of system 140 also may be configured to download real-time data relating to pump operation, as well as event logs stored during operation of implantable device 120. Based on the downloaded data, e.g., based on measurements made of the patient's intra-abdominal pressure, respiratory rate, and/or fluid accumulation, the software of system 140 optionally may be configured to alert the physician to a prediction or detection of a change in the patient's health for which an adjustment to the flow rate, volume, time and/or frequency of pump operation may be required. Finally, system 140 optionally may be configured to remotely receive raw or filtered operational data from a patient's handpiece 132 over a secure Internet channel. Further details of system 100 are describe in the above-incorporated U.S. patent.

Figure 3:
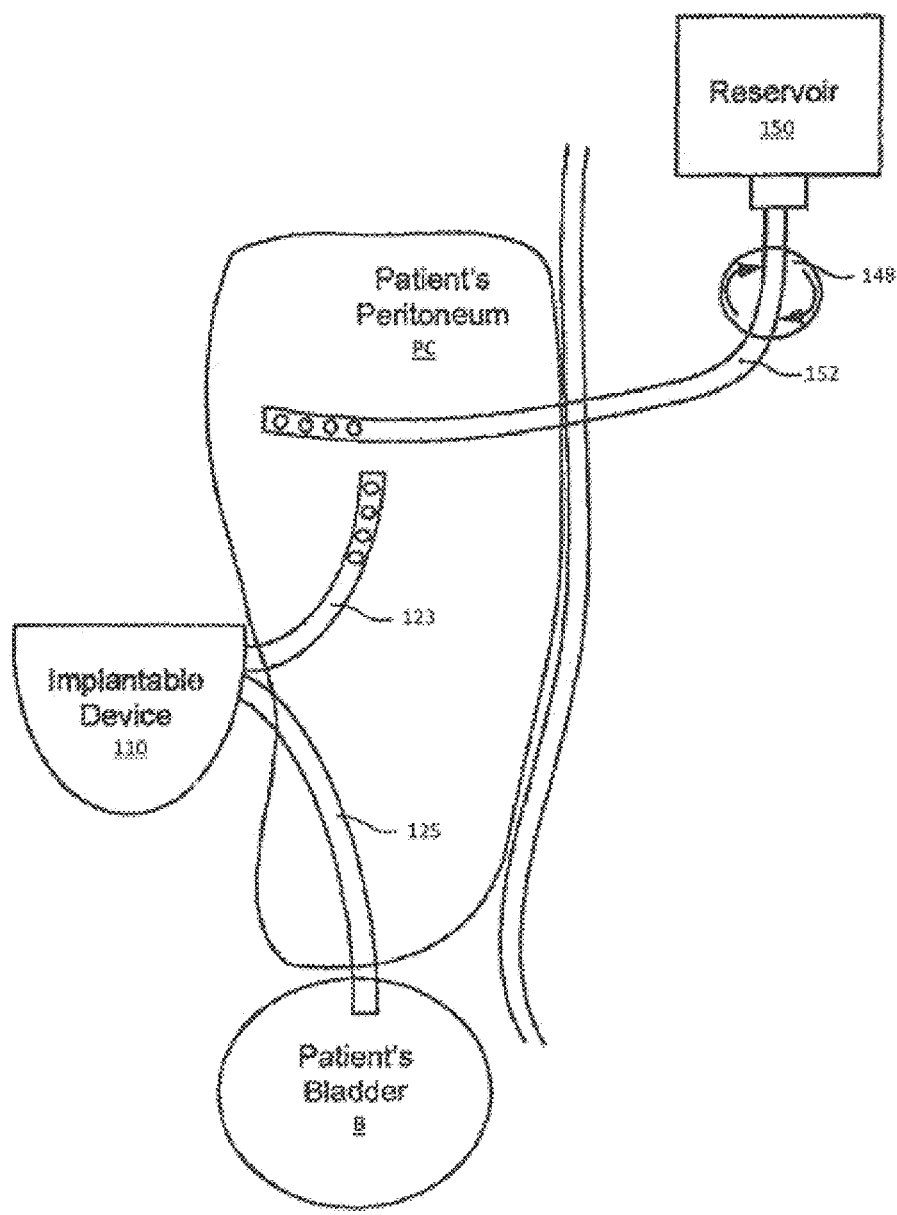
FIG. 3 is a schematic view of an exemplary arrangement for practicing the DSR therapy methods of the present invention using the implantable device of the system of FIG. 2.

FIG. 3 depicts implantable device 110 implanted within a patient's abdomen with the distal end of peritoneal catheter 123 disposed within the patient's peritoneal cavity PC and the distal end of bladder catheter 125 disposed in the patient's bladder B. Reservoir 150 of a first or second DSR solution is coupled to peritoneal infusion catheter 152 to deliver DSR solution from reservoir 150 into peritoneal cavity PC. Optional pump 148 may be coupled to infusion catheter 152 to accelerate instillation of DSR solution into the peritoneal cavity PC, or pump 148 may be omitted so that solution is infused via gravity.

In accordance with a preferred implementation of the invention, implantable device 120 is configured to move sodium-laden DSR infusate and osmotic ultrafiltrate from the peritoneal cavity to the bladder in quantities, intervals and flow rates selected to provide sufficient time for targeted amounts of sodium and/or fluid to accumulate in the DSR infusate. Treatment algorithms may be developed for the different DSR formulations and instilled volumes, different lengths of dwell period and different rates of removal to the bladder, to optimize serum sodium level as well as patient comfort. In general, pumping fluid from the peritoneal cavity for short but frequent intervals is expected to inhibit the accumulation of material on the interior lumens of catheters 123 and 125, and reduce the risk of tissue ingrowth. The fluid circuit of implantable device 120 may be configured to provide an average flow rate of between about 1 to 2.5 liters/hour, although much higher and lower flow rates are possible if needed. The pumping time, flow rate and volume, including the time the DSR infusate is allowed to remain in the peritoneal cavity, may be programmed by the physician using monitoring and control system 40 as required for a specific patient.

Figure 4:
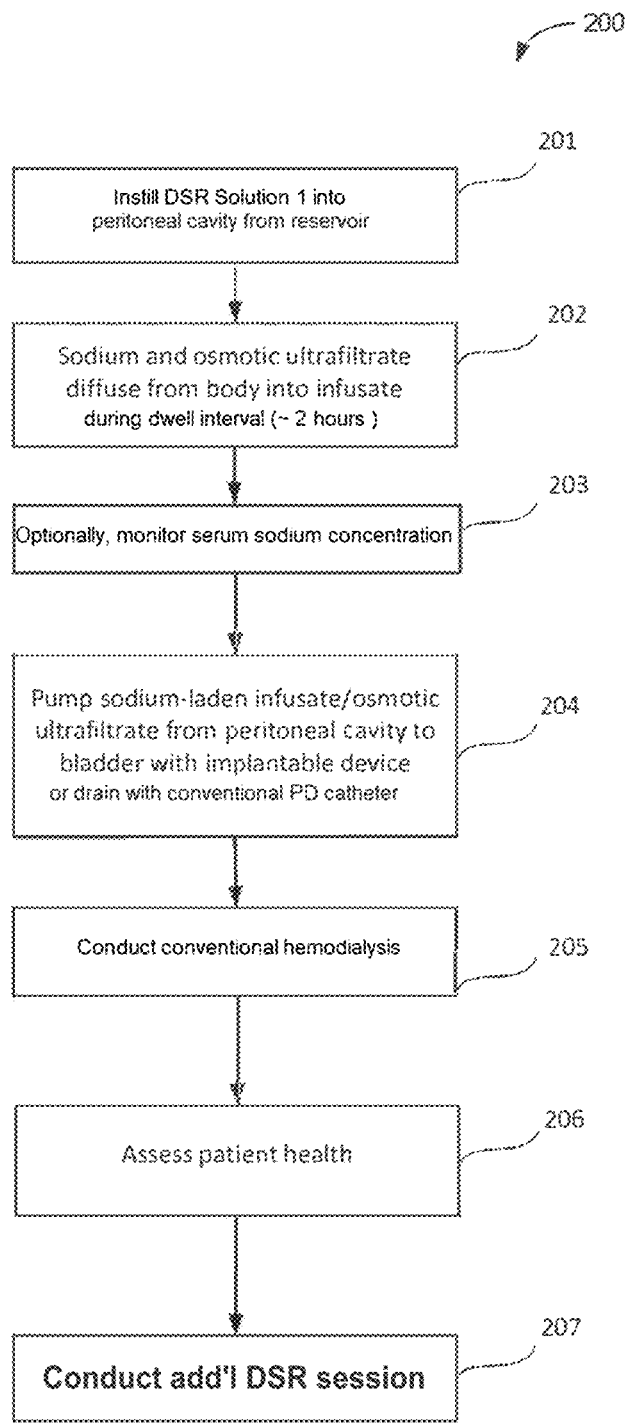
FIG. 4 illustrates steps of an exemplary method of using the DSR regimen of FIG. 1 in accordance with the principles of the present invention.

Referring now to FIG. 4, a method of treating a patient afflicted with severe renal dysfunction with a DSR regimen of the present invention is described. FIG. 4 describes an initial or follow-up DSR session, e.g., with DSR Solution or 2, as may be prescribed for on a patient-specific basis. Method 200 begins with instilling a DSR Solution in an amount of 0.25 liter to 1.5 liter or more into the peritoneal cavity of a patient from a reservoir, e.g., infusion bag 12 or 14 of FIG. 1 at step 201, using an external pump or gravity. At step 202, the DSR solution is permitted to remain in the peritoneal cavity for a specified dwell time, such as 2 hours, to cause excess sodium and fluid to migrate from the patient's body to the peritoneal cavity. At step 203, during the dwell time, the patient's serum sodium level optionally may be sampled to monitor the sodium level. Alternatively, expiration of the dwell time may be determined if the patient experiences discomfort from overextension of the abdomen.

At step 204, upon completion of the dwell time, sodium-laden DSR solution and ultrafiltrate is moved from the patient's body via a conventional peritoneal drainage catheter or by pumping it to the bladder using an implantable pump as described with respect to FIG. 2. If the fluid and sodium is pumped to the bladder, it may be excreted when the bladder is voided. Either way, removal of the DSR solution and ultrafiltrate reduces the amount of fluid and sodium from the body. At step 205, which may be a regularly scheduled dialysis session, the patient undergoes conventional hemodialysis or peritoneal dialysis to remove accumulated metabolic wastes and toxins. During this dialysis session, additional fluid or sodium may be removed to rebalance any residual fluid/sodium disequilibrium arising from the first DSR session. At step 206, the physician also may reassess the patient's need for loop diuretics, and make an appropriate adjustment in dosing a general assessment of the patient's health is conducted, including reduction in edema or fluid overload, cardiac and renal function, and serum sodium level. At step 207, an additional DSR session may be conducted using DSR Solution 2, and steps 202 to 206 repeated.

After the initial DSR session described in FIG. 4, it is expected that the patient's health metrics will stabilize, with reduced fluid overload and some improvement in renal function and/or enhanced efficacy of loop diuretics, if still used. To maintain these improvements, the patient may undergo one or more follow-up DSR sessions at step 207. The goal of these sessions may be to retain the renal improvements achieved from the initial DSR session, and/or to draw down additional amounts of non-osmotic sodium, as discussed above.

It is further contemplated that additional DSR sessions may periodically be scheduled to maintain patient health improvements resulting from the first and any prior follow-up DSR sessions. In addition, the physician may choose to revise the composition of the DSR infusate to titrate its ability to remove fluid and sodium specific to the needs of the patient. In this manner, it is expected that the physician may be able to prolong the benefits achieved during the prior DSR treatments, including reduced fluid overload, improved renal function and/or improved efficacy of loop diuretics, if still required. It is further hypothesized that a patient suffering end-stage renal disease who undergoes the regimen described above may arrest or possibly even reverse the course of the disease.

While various illustrative embodiments of the invention are described above, it will be apparent to one skilled in the art that various changes and modifications may be made therein without departing from the invention.

Preliminary Experimental Observations

Initial testing of the DSR infusate and methods of the present invention has been conducted to date in both a porcine model and in first-in-human trials. The results of that testing has provided remarkably successful and beneficial results, as described below, and shed additional light on the physiologic mechanisms involved.

Porcine Model Testing

In a first group of five pigs ("protocol refinement pigs"), the effect of infusing 1 liter of sodium-free DSR infusate into the peritoneal cavity of each pig was measured. The DSR infusate generally comprised purified water and dextrose, e.g., 10 grams per 100 ml of water, and was allowed to dwell in their peritoneal cavities for up to six hours. 5-25 micro curies of I-131 radiolabeled albumin was mixed into the infusate as a non-absorbable tracer to determine ultrafiltration kinetics without requiring serial drains of the abdomen. Throughout the dwell period, the fluid in the peritoneal cavities was sampled to determine total sodium removed and sodium concentration in the fluid accumulating in the peritoneal cavity as a function of time, and blood samples were taken as well. Specifically, in the 1½ hours after infusion of the DSR infusate, 3 ml blood sample and 2.5 ml fluid samples were taken every 15 minutes and analyzed. In the next 1½ hour period, blood and fluid samples were taken every ½ hour. And in the final 3 hours, additional blood and fluid samples were taken every hour. In addition, the total volume of fluid accumulated in the peritoneal cavity, consisting of sodium-laden DSR infusate and osmotic ultrafiltrate, was recorded as a function of time.

Figure 5A:
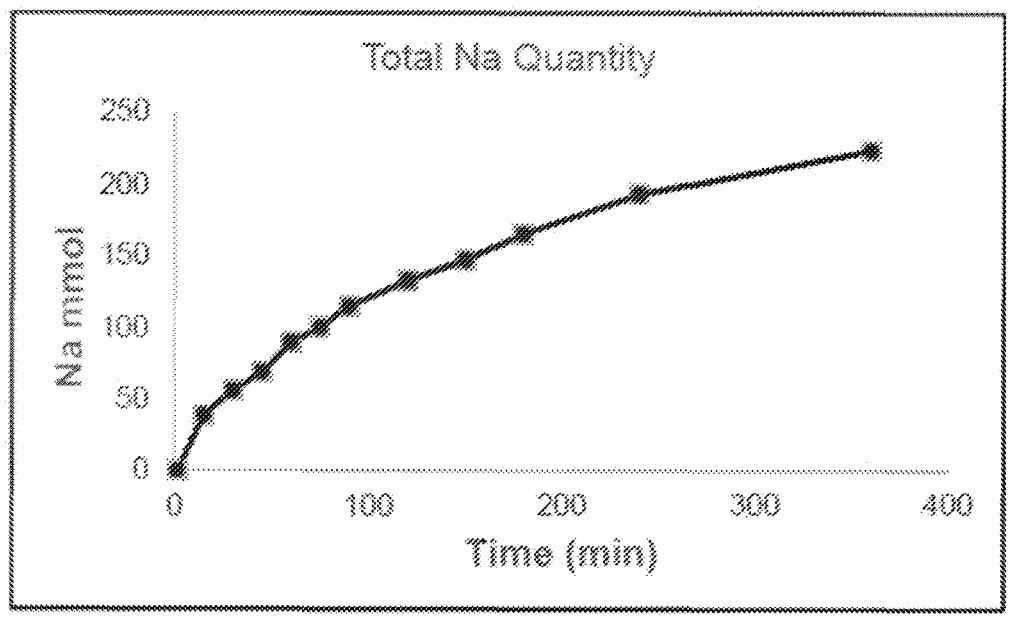
FIGS. 5A, 5B and 5C are graphs depicting the results of testing of the inventive DSR method on an initial group of five animals.
Figure 5B:
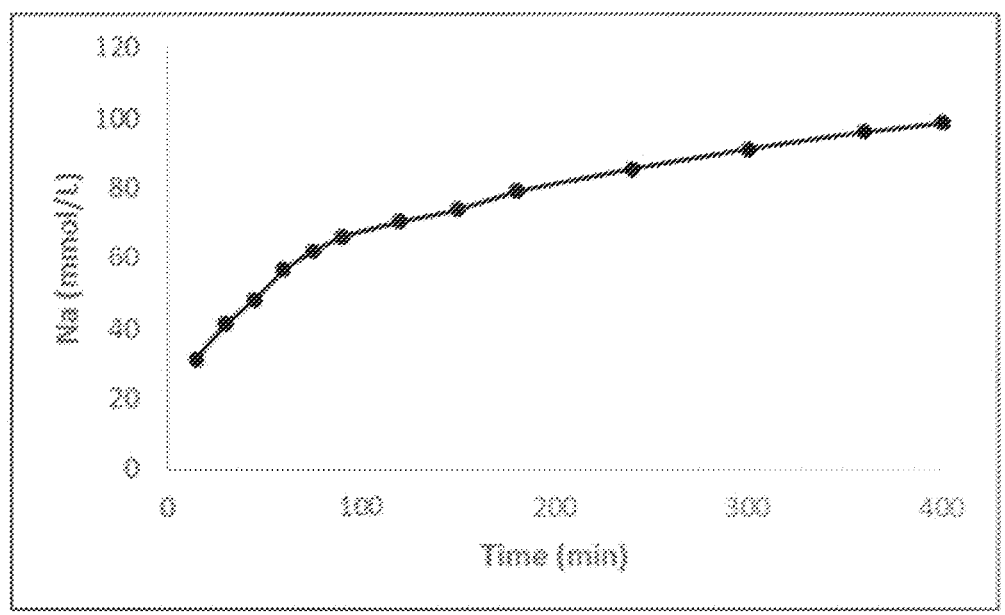
Figure 5C:
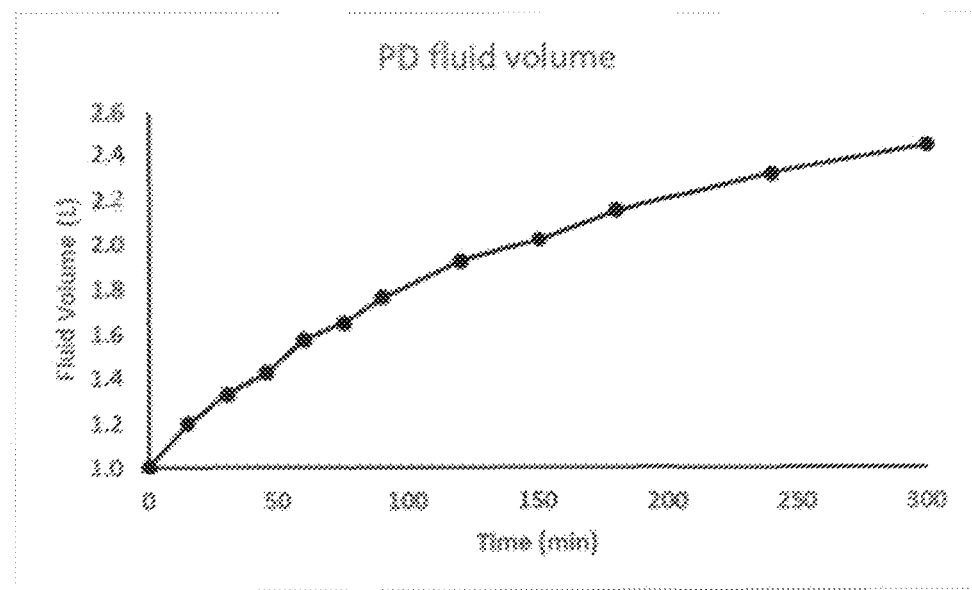

FIG. 5A shows the total amount of sodium removed as a function of dwell time for the first group of pigs, while FIG. 5B shows the sodium concentration in the samples removed from the peritoneal cavities as a function of time. FIG. 5C depicts the total volume of fluid accumulated in the peritoneal cavities of the first group of pigs. As shown in FIG. 5C, after two hours, infusion of 1 liter of DSR infusate induced about 1 liter of osmotic filtrate to accumulate in the peritoneal cavity.

In a second group of ten pigs ("protocol pigs"), 1 liter of DSR infusate was infused in the peritoneal cavities of each pig for a two-hour dwell period. Throughout the dwell period serum sodium, serum osmolality, plasma osmolality and glucose levels of the pigs were periodically measured by taking 6 ml blood samples every ½ hour. Total osmolality, glucose osmolality and non-glucose osmolality of the fluid accumulating in the peritoneal cavities were periodically measured during the dwell period using the foregoing samples. After completion of the dwell period, the total volume of fluid drained from the peritoneal cavity and the total amount of sodium removed, was measured.

Figure 6A:
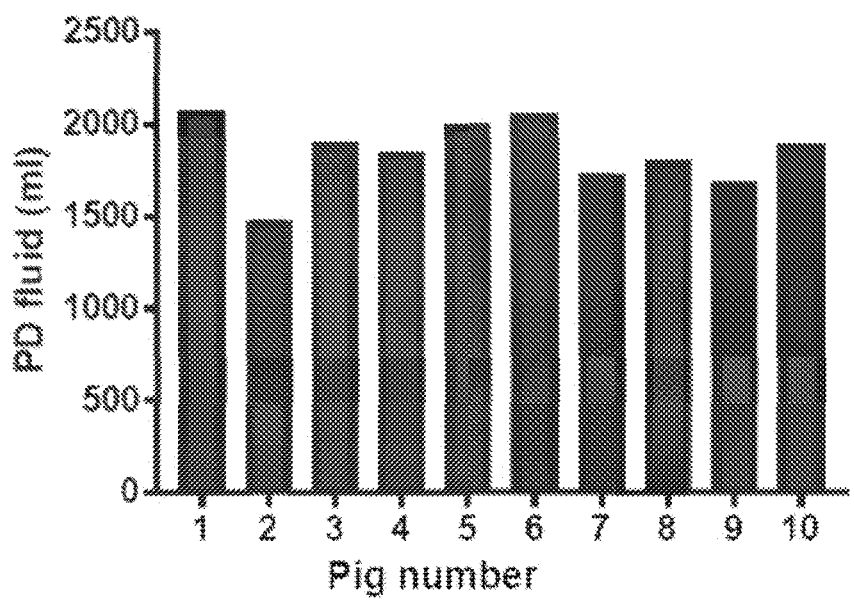
FIGS. 6A to 6F are graphs depicting the results of testing of the inventive DSR method on a follow-up group of ten animals.
Figure 6B:
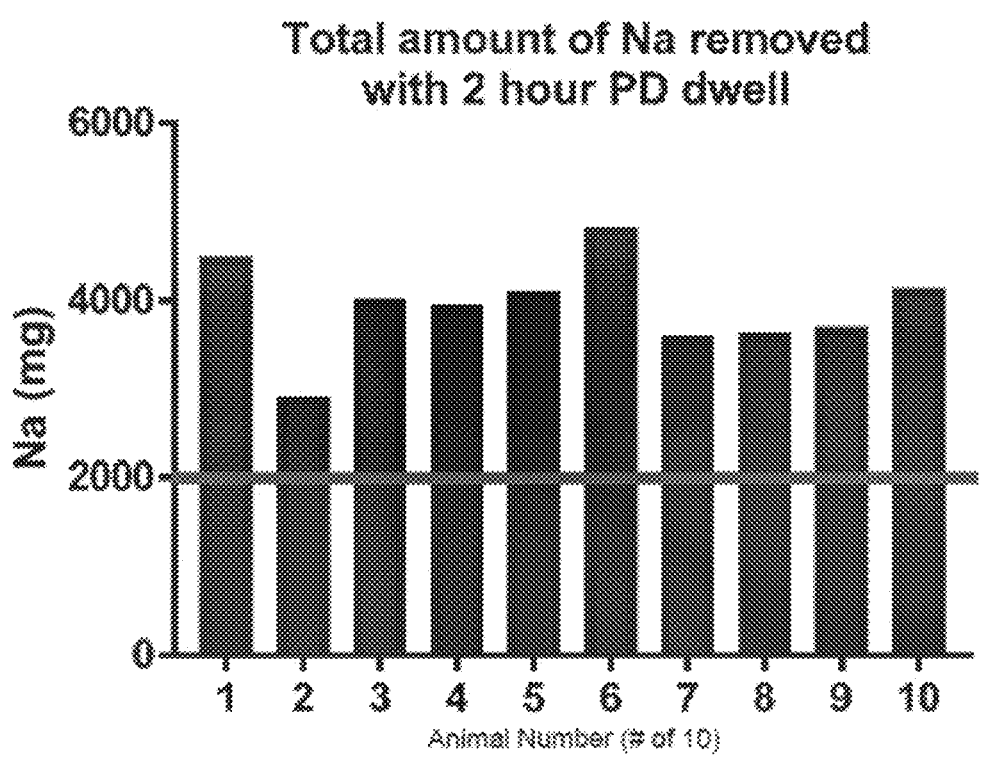
Figure 6C:
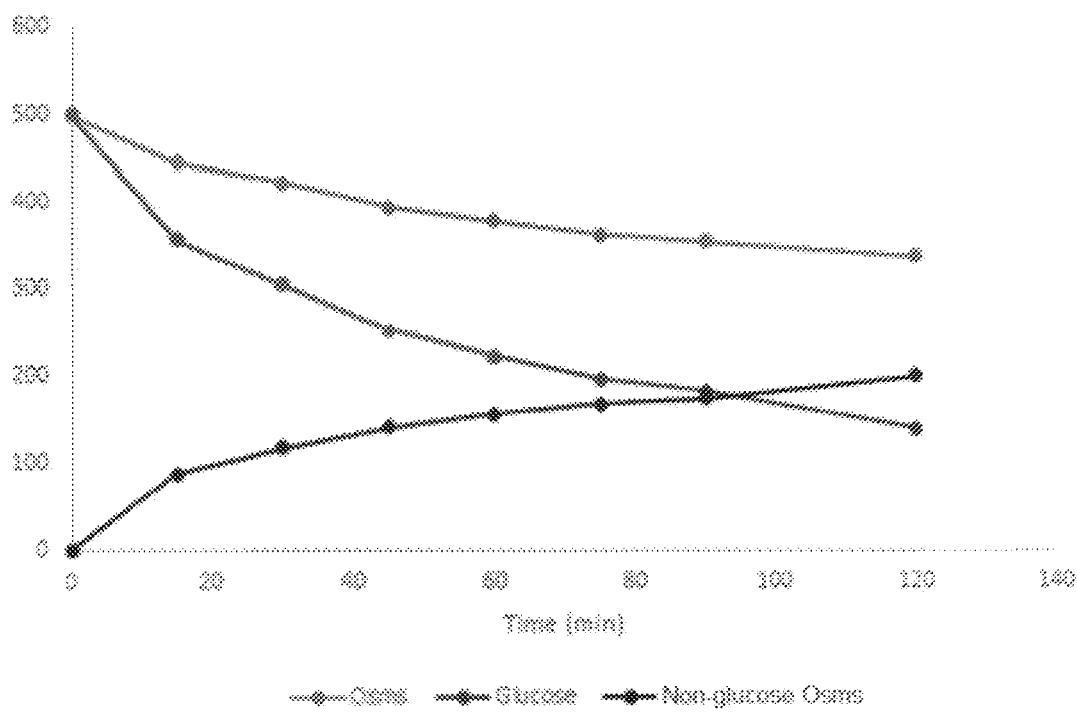
Figures 6D, 6E:
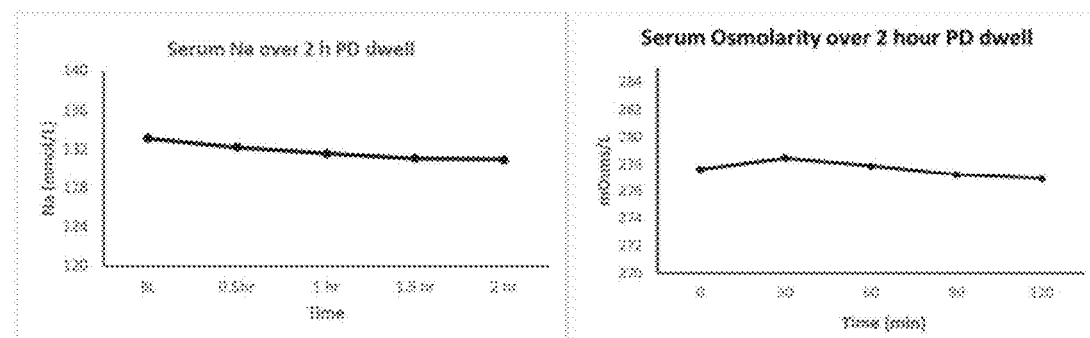
Figure 6F:
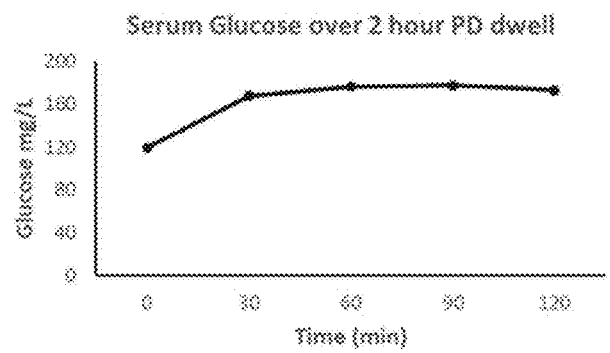

FIG. 6A is a chart showing the total fluid volume removed from the peritoneal cavity of each protocol pig after a two-hour dwell. FIG. 6B shows the total amount of sodium removed from the peritoneal cavity of each protocol pig after a two-hour dwell. FIG. 6C shows the evolution of total osmolality, glucose osmolality, and non-glucose osmolality for samples of fluid from the peritoneal cavities of the protocol pigs throughout the two-hour dwell period. FIGS. 6D, 6E and 6F show the evolution of serum sodium, serum osmolality, and serum glucose, respectively, for the protocol pigs throughout the two-hour dwell period. The foregoing results demonstrate that DSR infusates can remove a clinically relevant amount of sodium, e.g., about 4 g, with a single administration of 1 liter of DSR infusate and a two-hour dwell, but with clinically negligible impact on serum sodium levels. That amount of removed sodium is generally equivalent to two days of recommended sodium consumption, which will induce the elimination of stored fluid via urination and direct removal of a significant (1 liter with the studied parameters) accumulation of osmotic ultrafiltrate from the peritoneal cavity. And as shown in FIGS. 6D, 6E and 6F, the single administration of DSR infusate with a two-hour dwell is expected to be very safe, as serum sodium level and serum osmolality remained stable throughout the period with only an expected and clinically manageable increase of serum glucose concentration.

Figures 7A, 7B, 7C:
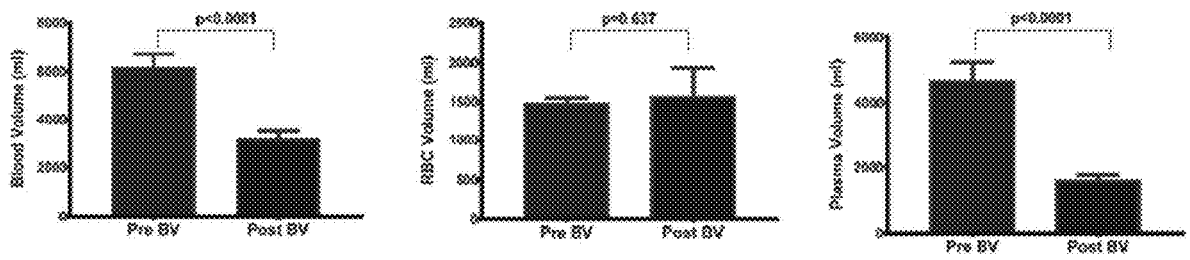
FIGS. 7A to 7C are graphs depicting changes to blood volume, red blood count, and plasma volume for a subgroup of the second group of animals after consecutive applications of the inventive DSR method.

FIGS. 7A-7C depicts the measurements for a number of blood volume markers in a sub-group of five of the protocol pig population both before and after repeated application of a 10 weight percent dextrose DSR solution. FIG. 7A shows almost a ½ reduction in the total blood volume of the protocol pigs after five cycles of DSR treatment. As expected, FIG. 7B shows virtually no impact of the DSR method on the total volume of red blood cells. However, FIG. 7C shows that there is a reduction in plasma volume of approximately 60%. Accordingly, as depicted in FIGS. 7A-7C, repeated use of a DSR solution can achieve a significant reduction in blood volume by reducing plasma volume. This also demonstrates that a DSR solution can be used to eliminate different levels of fluid overload.

First-In-Man Feasibility Studies

The assignee of the present invention sought and obtained permission from an investigational review board to conduct a first trial to assess the feasibility of removing sodium from patients with a single dose of DSR solution, and a second follow-up study to assess safety and tolerance to serial DSR sessions. The first trial was conducted with ten patients with end-stage renal disease who regularly underwent peritoneal dialysis with pre-existing peritoneal catheters. In the second follow-up study, the DSR solution was instilled via subcutaneous ports and after a dwell time, removed via an implantable pump as described with respect to FIG. 2. In both trials, a DSR solution of 10 weight percent dextrose in sterile water as a peritoneal infusate. The details and results of these initial trials are described with respect to FIGS. 8 through 11.

In the first study, patients receiving peritoneal dialysis for end-stage renal disease with functioning peritoneal dialysis catheters underwent randomization and crossover to open-label DSR solution (sodium-free 10% dextrose) or standard peritoneal dialysis solution (Dianeal Low-Calcium with 4.25% dextrose; Baxter; Deerfield, Ill.), each separated by 1 week. This phase 1 study was conducted in patients receiving prevalent peritoneal dialysis rather than normal subjects to avoid the risk of placing a peritoneal dialysis catheter would pose to a normal subject. Inclusion criteria were the following: actively undergoing peritoneal dialysis with a functioning peritoneal dialysis catheter implanted less than 3 years, patient age greater than 18 years and judged by the treating nephrologist to be at or above optimal volume status (i.e., not dehydrated). Exclusion criteria were uncontrolled diabetes mellitus with frequent episodes of severe hyperglycemia; systolic blood pressure<100 mm Hg; serum sodium<130 mEq/L; one or more episodes of peritonitis in the previous 6 months or active infection of the peritoneal dialysis catheter; anemia with hemoglobin<8 g/dL; serum bicarbonate<18 mEq/L; anuric renal failure; inability to give written informed consent or to follow the study protocol; and pregnant or lactating.

A 4.25% dextrose peritoneal dialysis solution was selected as the comparison solution because it is the most effective marketed peritoneal dialysis solution for fluid/sodium removal and has an osmolarity similar to that of 10% dextrose. Before instillation of the study fluid, there was a 30-minute drain of the abdomen with the patient assuming multiple positions during this time to ensure as complete drainage as possible. Given that this was a dialysis population with a tendency to develop acidosis, all patients were given 30 mEq sodium citrate/citric acid by mouth. Next, 1 L of either DSR solution or standard peritoneal dialysis solution was infused into the peritoneum and left to dwell for 2 hours. The intraperitoneal volume was determined longitudinally using the indicator dilution technique with I-131-radiolabeled albumin (Daxor Inc), in addition to direct measurement of drained fluid at the end of the dwell. Vital signs, blood (every 30 minutes), and peritoneal fluid (every 15 minutes) were obtained serially throughout the protocol. Patients in the DSR group were given 50% of the ultrafiltration volume back at the end of the dwell in the form of intravenous normal saline to replace sodium/volume losses. The primary end point was safety/tolerability, defined as completion of the 2-hour dwell without significant discomfort or adverse events. The secondary efficacy end point was the difference in sodium removal between the DSR solution and standard peritoneal dialysis solution.

Ten patients completed the crossover study. The baseline characteristics for these patients are presented in the Table below.

| Characteristics | All Patients |
|---|---|
| Demographics | |
| Age, y | 54 ± 12 |
| Male sex, n (%) | 70 (7) |
| White race, n (%) | 50 (5) |

| Characteristics | All Patients |
|---|---|
| Comorbidities, n (%) | |
| Diabetes mellites | 30 (3) |
| Hypertension | 90 (9) |
| Heart failure | 10 (1) |
| Physical examination | |
| Weight, lb, mean ± SD | 251 ± 72 |
| SBP, mm Hg | 144 (132-156) |
| Peritoneal Dialysis variables | |
| Peritoneal Dialysis Catheter vintage, years | 1.3 ± 0.9 |
| Automated Peritoneal Dialysis use, n (%) | 100 (10) |
| Icodextrin use, n (%) | 30 (3) |
| Last fill, n (%) | 40 (4) |
| Type of renal disease, n (%) | |
| Diabetic nephropathy | 2 (20) |
| Hypertensive nephrosclerosis | 1 (10) |
| Excessive NSAID use | |
| Systemic lupus erythematosus | |
| Nephrotic syndrome | |
| Immunoglobulin A nephropathy | |
| Granulomatosis with polyangitis-ESRD | |
| Polycystic kidney disease | |
| Failed allograft | |
| Medications, n (%) | |
| Antihypertensives | 90 (9) |
| Loop diuretics | 60 (6) |
| Calcium channel blockers | 60 (6) |
| β-Blockers | 50 (5) |
| ACE inhibitors | 30 (3) |
| Thiazide-type diuretics | 20 (2) |
| Angiotensin II receptor blockers | 20 (2) |
| α-Agonists | 10 (1) |
| Insulin | 20 (2) |
| Laboratory values, mean ± SD | |
| Sodium, mmol/L | 137.9 ± 3.5 |
| Hemoglobin, g/dL | 10.2 ± 1.3 |
| BUN, mmol/L | 54 ± 19 |
| Calcium, mmol/L | 1.11 ± 0.14 |
| Potassium, mmol/L | 4.2 ± 0.4 |

The primary end point, defined as completion of the 2-hour dwell without significant discomfort or adverse events, was met in all 10 patients. Overall, the treatment was well tolerated, with 2 of 10 patients reporting mild and short-duration cramping during instillation of the 10% dextrose solution; one of those patients had similar cramping during the standard peritoneal dialysis solution instillation. There were no significant differences in blood pressure or peak heart rate between the 2 groups. Changes in plasma glucose were larger with the 10% dextrose solution compared with standard peritoneal dialysis solution, with the most pronounced differences early in the dwell. However, differences in plasma glucose completely resolved after draining of the solution. No patients developed severe hyperglycemia at any time point in either group. The relative glucose absorption was the same between the 10% dextrose and standard peritoneal dialysis solution; however, given the larger absolute amount of glucose in 10% dextrose, the absolute quantity of glucose absorbed was larger with 10% dextrose.

Serum sodium was not different between groups. Removal of off-target nonsodium electrolytes with DSR such as potassium (5.5±1.1 mmol), magnesium (1.7±2.5 mmol), phosphorus (1.9±0.6 mmol), and calcium (1.6±0.3 mmol) was negligible, and plasma electrolyte and chemistry parameters were stable throughout the dwell. As shown in FIG. 8A, the secondary efficacy outcome of superior sodium removal with sodium-free 10% dextrose (4.5±0.4 g) compared with standard peritoneal dialysis solution (1.0±0.3 g) was met (P<0.001). In addition to a substantially higher average sodium clearance, the consistency of sodium removal was excellent. The absolute variability between individual patients' sodium removal and the average sodium removal was similar between DSR and standard peritoneal dialysis solution, as depicted in FIG. 8B. However, because the total sodium removed in standard peritoneal dialysis solution was substantially lower, the relative variability between individuals was much higher with standard peritoneal dialysis solution, ranging from 8% to 75% of the average total sodium removal compared with 2% to 18% in patients receiving DSR. Fluid removal was also greater with sodium-free 10% dextrose, also with a high degree of consistency across patients.

The primary finding from the first human trial is that substantial sodium removal via the peritoneal membrane is feasible. In particular, it was observed that using 1 liter of sodium free 10% dextrose solution, leveraged both diffusive and convective forces, and could remove>4 g sodium in 2 hours. The DSR therapy was well tolerated, with limited effect on plasma electrolyte levels, minimal off-target solute removal, and freedom from discomfort in the majority of human participants. The sodium removal was scalable, with substantially larger quantities of sodium removed by increasing the volume of 10% dextrose cycled into the peritoneal space.

In the second study, the primary objective was to assess the safety and tolerability of serial treatment with DSR therapy in chronic stable diuretic resistant heart failure patients. A secondary objective of this study was to assess the impact of serial treatment with DSR therapy on parameters of renal function and diuretic response. In this study, DSR solution was instilled into the patient's peritoneal cavities via subcutaneous port. The implantable pump system developed by the assignee of the present application, Sequana Medical, N.V., was employed to move fluid from the patients' peritoneal cavities to their bladders. Ten patients were admitted into the second study, in accordance with the following criteria:

Inclusion Criteria:
1. eGFR>30 ml/min/14.73 m2
2. Diagnosis of heart failure with one of the following:
   a. nt-proBNP>400 pg/ml (or BNP>100 pg/ml) and oral diuretic dose>80 mg furosemide equivalents OR
   b. Oral diuretic dose>120 mg furosemide equivalents
3. Stable diuretic dose for 30 days
4. Systolic blood pressure>100 mmHg
5. Determined by treating provider to be at optimal volume status Exclusion Criteria:
1. Serum sodium<135 mEq/L
2. Severe hyperkalemia or baseline plasma potassium>4.5 mEq/L
3. History of significant bladder dysfunction expected to interfere with ability of subject to tolerate DSR pumping into bladder
4. Uncontrolled diabetes with frequent hyperglycemia or Type 1 diabetes The second study ran for a total of 6 weeks, plus a two-week follow-up. After screening, ten patients were implanted with the Alfapump® implantable pump described in FIG. 2 about two weeks prior to initiation of the trial. Three days before the DSR trial was begun, each patient was given an intravenous administration of 40 mg of furosemide, followed by a 6-hour timed urine collection. At the outset of the DSR trial, all loop diuretics were stopped. During the following two weeks, the patients were resident in-hospital with diets controlled at 3 grams of sodium per day for the first week and 5 grams of sodium the second week. Patients then were permitted to return home. During the two week in-hospital stay and the following four weeks, the patients underwent DSR sessions three times a week using a 10 weight percent dextrose DSR solution. At the conclusion of the six weeks of DSR sessions, the patients again underwent a diuretic challenge with intravenous administration of 40 mg of furosemide, followed by a 6-hour timed urine collection.

Baseline characteristics for the group is set forth in the table below:

| N = 8 | Result | Min:Max |
|---|---|---|
| Age - Years (Mean ± SD) | 61.9 ± 8.5 | 49:77 |
| Male - % | 100 | N/A |
| Height - cm (Mean ± SD) | 172.8 ± 5.7 | 163:182 |
| Weight - kg (Mean ± SD) | 75.4 ± 17.7 | 53.0:107.8 |
| BMI - kg/m² (Mean ± SD) | 25.2 ± 4.8 | 19.1:32.6 |
| Ejection Fraction - % (Mean ± SD) | 24.4 ± 3.1 | 20:28 |
| Nt-proBNP - pg/mL (Mean ± SD) | 4588.9 ± 2945.1 | 1536:8831 |
| eGFR - ml/min/1.73 m² (Mean ± SD) | 68 ± 19 | 37:96 |
| Hematocrit - % (Mean ± SD) | 43.9 ± 7.48 | 32.5:55.2 |
| Furosemide equivalents - mg (Mean ± SD) | 322.5 ± 263.3 | 80:800 |

By the conclusion of the six-week study, all patients had remained off loop diuretics for the entire period. A neutral sodium balance was achieved (−1.3 grams) during the 2 week in-hospital period. Stable weight over the duration of the study also was achieved (75.6 to 75.5 kg). Most patients had down titration of DSR therapy to maintain constant weight; the volume of 10% dextrose DSR solution was on average 750±348 ml/treatment.

Figures 11, 12:
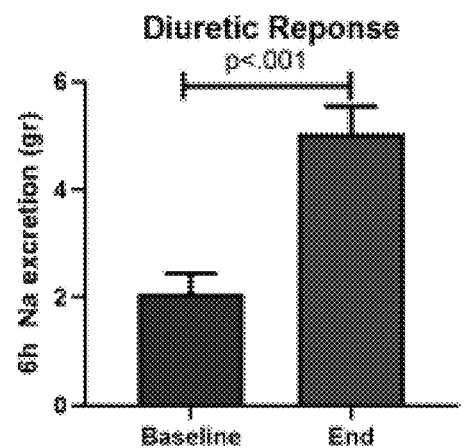
FIG. 11 is a bar chart showing the improvement in diuretic response in the second trial.
FIG. 12 is a table showing a durable effect post DSR-treatment for patients who experienced a substantial reduction in need for diuretic drugs following the second trial.

Results of the study are presented in FIGS. 9 to 12. In particular, as shown in FIGS. 9A and 9B, the study participants experienced a significant reduction in measured N-terminal-pro B-type natriuretic peptide ("NT-proBNP") and creatinine levels, indicating improvement in cardio-renal function. FIGS. 10A, 10B and 10C depict the temporal trends of improvement for the study patients over the six-week period. FIG. 11 depicts improvement in the patients' response to loop diuretic between the trial outset and after six weeks of DSR sessions, showing a 3-fold increase in urine output. FIG. 12 is a table reporting the results of follow-up evaluations with eight of the patients in the study, and indicates that the effect of the DSR therapy in reducing diuretic resistance was durable, with patients experiencing a reduction between 89% and 50% of their daily diuretic dosing at 10 to 12 months following their last DSR session, with at least one patient ceasing the use of a diuretic entirely.

The second human study therefore demonstrated that six weeks of DSR therapy, using an implantable pump to remove the DSR solution and ultrafiltrate, was overall well tolerated and successfully maintained a neutral sodium balance and stable body weight, despite complete withdraw of loop diuretics. The study also showed significant benefit to cardio-renal function, as observed by meaningful improvement in NT-proBNP and renal function. In addition, diuretic resistance substantially and durably improved.

Based on the results of initial human trials, which employed a single composition of DSR infusate, e.g., 10 weight percent dextrose, it is theorized that use of multiple compositions in a regimen interspersed with the patient's regularly conducted dialysis sessions may substantially enhance long-term efficacy of loop diuretics, permit the administration of reduced doses, and arrest and possibly reverse renal disease and heart failure. As discussed above, use of multiple DSR compositions may enable a patient's physician to gradually reduce fluid and sodium overload over a period of several weeks to months, and thereby establish an improved sodium and fluid metabolism for the patient that ameliorates both severe renal dysfunction and heart failure.

While various illustrative embodiments of the invention are described above, it will be apparent to one skilled in the art that various changes and modifications may be made therein without departing from the invention. For example, pump system 1 may be ordered differently and may include additional or fewer components of various sizes and composition. The appended claims are intended to cover all such changes and modifications that fall within the true spirit and scope of the invention.

What is claimed is:

1. An infusate regimen for use in removing excess sodium and fluid from a patient having fluid overload or severe renal dysfunction, the infusate regimen comprising:
   a first direct sodium removal ("DSR") infusate formulated to be administered by infusion into, and removal from, a peritoneal cavity of a patient, the first DSR infusate having a first osmolality in which an aqueous solution contains a sodium concentration equal to or less than 35 meq/L and at least one of zero to 50 grams of dextrose per 100 ml of aqueous solution, 0.5 to 50 grams of icodextrin per 100 ml of aqueous solution, 0.5 to 50 grams of a high molecular weight biocompatible polymer having an average molecular weight greater than 10,000 Daltons per 100 ml of aqueous solution, or solutions containing any one or more of 0.5 to 50 grams of xylitol, glycerol, hyperbranched polyglycerol, sorbitol, carnitine, taurine, amino acids, urea, polyacrylate, polyethyleneimine, or stevioside per 100 ml of aqueous solution, or any combination thereof.

2. The infusate regimen of claim 1, further comprising:
   a second DSR infusate formulated to be administered by infusion into, and removal from, the peritoneal cavity of the patient, the second DSR infusate having a second osmolality in which an aqueous solution contains a sodium concentration equal to or less than 35 meq/L and at least one of zero to 50 grams of dextrose per 100 ml of aqueous solution, 0.5 to 50 grams of icodextrin per 100 ml of aqueous solution, or 0.5 to 50 grams of a high molecular weight biocompatible polymer having an average molecular weight greater than 10,000 Daltons per 100 ml of aqueous solution, or solutions containing any one or more of 0.5 to 50 grams of xylitol, glycerol, hyperbranched polyglycerol, sorbitol, carnitine, taurine, amino acids, urea, polyacrylate, polyethyleneimine or stevioside per 100 ml of aqueous solution, or any combination thereof, wherein the second osmolality is different than the first osmolality.

3. The infusate regimen of claim 1, wherein the first DSR infusate has an osmolality and sodium concentration selected to induce a steep sodium gradient between a patient's blood serum sodium level and the first DSR infusate when instilled into the peritoneal cavity during a first dwell period.

4. The infusate regimen of claim 2, wherein the second DSR infusate has an osmolality and sodium concentration selected to induce a shallow sodium gradient between the patient's blood serum sodium level and the second DSR infusate when instilled into the peritoneal cavity during a second dwell period.

5. The infusate regimen of claim 1, wherein the first DSR infusate is sodium-free.

6. The infusate regimen of claim 2, wherein the first DSR infusate or second DSR infusate further comprises an electrolyte selected from among a magnesium salt and a calcium salt.

7. The infusate regimen of claim 2, wherein the first DSR infusate or second DSR infusate further comprises at least one of: an antimicrobial agent, an antifungal agent, and a buffering agent.

8. The infusate regimen of claim 1, wherein the first DSR infusate is formulated to be sufficiently nonviscous that the infusate may be instilled into the peritoneal cavity from a reservoir via gravity feed.

9. The infusate regimen of claim 2, wherein the second DSR infusate is formulated to be sufficiently nonviscous that the infusate may be instilled into the peritoneal cavity from a reservoir via gravity feed.

10. The infusate regimen of claim 2, wherein the each of the first DSR infusate and the second DSR infusate are formulated to be instilled into a patient's peritoneal cavity in an amount between 0.25 liter and 2.0 liter per DSR session.

11. A method of reducing fluid overload in a patient suffering from severe renal dysfunction or heart failure, the method comprising:
    administering a first DSR infusate having no or low sodium and a first osmolality into a peritoneal cavity of a patient to induce sodium and osmotic ultrafiltrate to accumulate with the first DSR infusate in the peritoneal cavity during a first dwell period, wherein the first DSR infusate has a first osmolality in which an aqueous solution contains a sodium concentration equal to or less than 35 meq/L and at least one of zero to 50 grams of dextrose per 100 ml of aqueous solution, 0.5 to 50 grams of icodextrin per 100 ml of aqueous solution, 0.5 to 50 grams of a high molecular weight biocompatible polymer having an average molecular weight greater than 10,000 Daltons per 100 ml of aqueous solution, or solutions containing any one or more of 0.5 to 50 grams of xylitol, glycerol, hyperbranched polyglycerol, sorbitol, carnitine, taurine, amino acids, urea, polyacrylate, polyethyleneimine, or stevioside per 100 ml of aqueous solution, or any combination thereof; and
    removing the first DSR infusate, sodium and osmotic ultrafiltrate from the peritoneal cavity of the patient by pumping fluid with an implantable pump from the peritoneal cavity to a bladder of the patient, for subsequent elimination by urination.

12. The method of claim 11, further comprising:
    administering a second DSR infusate having no or low sodium and a second osmolality, different than the first osmolality, into the peritoneal cavity of the patient to induce sodium and osmotic ultrafiltrate to accumulate with the second DSR infusate in the peritoneal cavity during a second dwell period, wherein the second DSR infusate has a second osmolality in which an aqueous solution contains a sodium concentration equal to or less than 35 meq/L and at least one of zero to 50 grams of dextrose per 100 ml of aqueous solution, 0.5 to 50 grams of icodextrin per 100 ml of aqueous solution, or 0.5 to 50 grams of a high molecular weight biocompatible polymer having an average molecular weight greater than 10,000 Daltons per 100 ml of aqueous solution, or solutions containing any one or more of 0.5 to 50 grams of xylitol, glycerol, hyperbranched polyglycerol, sorbitol, carnitine, taurine, amino acids, urea, polyacrylate, polyethyleneimine or stevioside per 100 ml of aqueous solution, or any combination thereof; and removing the second DSR infusate, sodium and osmotic ultrafiltrate from the peritoneal cavity of the patient to the bladder.

13. The method of claim 12, wherein removing the second DSR infusate, sodium and osmotic ultrafiltrate from the peritoneal cavity of the patient comprises pumping fluid from the peritoneal cavity to a bladder of the patient with an implantable pump.

14. The method of claim 12, further comprising, between administering a first DSR infusate and administering a second DSR infusate or thereafter, adjusting a serum sodium level of the patient by conducting hemodialysis or peritoneal dialysis.

15. The method of claim 12, wherein administering a first DSR infusate or a second DSR infusate comprises introducing a DSR infusate containing dextrose or Icodextrin or combinations thereof.

16. The method of claim 12, wherein administering a first DSR infusate or a second DSR infusate comprises introducing a DSR infusate via a subcutaneous port or a conventional peritoneal dialysis catheter.

17. The method of claim 11, further comprising monitoring a serum sodium level of the patient during the first dwell period.

18. The method of claim 11, wherein the first DSR infusate has an osmolality and sodium concentration selected create a steep sodium gradient between a patient's blood serum sodium level and the first DSR infusate when instilled into the peritoneal cavity during the first dwell period.

19. The method of claim 12, wherein the second DSR infusate has an osmolality and sodium concentration selected to create a shallow sodium gradient between a person's blood serum sodium level and the second DSR infusate when instilled into the peritoneal cavity during the second dwell period.

20. The method of claim 12, wherein administering each of the first DSR infusate and the second DSR infusate comprises instilling into the patient's peritoneal cavity an amount between 0.25 liter and 2.0 liter of fluid per DSR session.

* * * * *